US008653285B2

(12) United States Patent
Higashiura et al.

(10) Patent No.: US 8,653,285 B2
(45) Date of Patent: Feb. 18, 2014

(54) AMINOPROPYLIDENE DERIVATIVE

(75) Inventors: Kunihiko Higashiura, Kato (JP); Takashi Ogino, Kato (JP); Taizo Ito, Kato (JP); Koji Kunimasu, Kato (JP); Kazuhito Furukawa, Kato (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 487 days.

(21) Appl. No.: 13/055,780

(22) PCT Filed: Jul. 31, 2009

(86) PCT No.: PCT/JP2009/063645
§ 371 (c)(1),
(2), (4) Date: Jan. 25, 2011

(87) PCT Pub. No.: WO2010/013805
PCT Pub. Date: Feb. 4, 2010

(65) Prior Publication Data
US 2011/0124856 A1  May 26, 2011

(30) Foreign Application Priority Data

Aug. 1, 2008  (JP) .................................. 2008-199648
May 27, 2009  (JP) .................................. 2009-127385

(51) Int. Cl.
*C07D 313/08* (2006.01)
*C07D 333/50* (2006.01)
*A61K 31/38* (2006.01)
*A61K 31/335* (2006.01)

(52) U.S. Cl.
USPC .............. 549/354; 549/43; 514/443; 514/450

(58) Field of Classification Search
USPC .............................. 549/354, 43; 514/443, 450
See application file for complete search history.

(56) References Cited

U.S. PATENT DOCUMENTS

| 3,770,728 | A  | 11/1973 | Bourquin et al. |
| 5,116,863 | A  | 5/1992  | Oshima et al. |
| 7,589,103 | B2 | 9/2009  | Carson et al. |
| 2009/0298867 | A1 | 12/2009 | Carson et al. |
| 2010/0331365 | A1 | 12/2010 | Higashiura et al. |

FOREIGN PATENT DOCUMENTS

| EP | 2067777 A1 | 12/2010 |
| FR | 1502857 | * 11/1967 |
| GB | 1445 127 | 8/1976 |
| JP | A-47-06780 | 1/1972 |
| JP | A-49-069677 | 7/1974 |
| JP | A-63-010784 | 1/1988 |
| JP | A-2008-019121 | 1/2008 |
| WO | WO 2005/003131 A1 | 1/2005 |
| WO | WO 2008/038711 A1 | 4/2008 |

OTHER PUBLICATIONS

International Search Report issued in PCT/JP2009/063645 on Sep. 29, 2009.
PCT Written Opinion issued in PCT/JP2009/063645 on Sep. 29, 2009.
Karel Sindelar et al. ,"Antihistamine Substances. Tricyclic Analogues of N-(4,4-Diphenyl-3-Butene-1-YL) Nipecotic Acid and Some Related Compounds", Collect. Czech. Chem. Commun., (1994), 667-674. (vol. 59).
Von J.M. Bastian et al., "Beiträge zur Chemie des 4,5-ihydro-10H-benzo [5,6] cyclohepta [1,2-b] thiophens", Helvetica Chimica Acta, (1971), 277-282, (vol. 54).
Von Erwin Waldvogel et al., "Untersuchungen über synthetische Arzneimittel 9- und 10-Oxo-Derivate von 9,10-Dihydro-4H-benzo [4,5] cyclohepta-[1,2-b] thiophenen", Helvetica Chimica Acta, (1976), 866-877, (vol. 59).
Steven R. Schow et al., "Utility of the Wittig Reaction for the Construction of Side Chains of Steroids Starting from Pregnenolone", J. Org. Chem., (1979), 3760-3765, (vol. 44).
Etsuo Ohshima et al., "Synthesis and Antiallergic Activity of 11-(Aminoalkylidene)-6,11-dihydrodibenz[b,e] oxepin Derivatives", J. Med. Chem., (1992), 2074-2084, (vol. 35).
Morten Jørgensen et al., "Efficient Synthesis of α-Aryl Esters by Room-Temperature Palladium-Catalyzed Coupling of Aryl Halides with Ester Enolates", J. Am. Chem. Soc., (2002), 12557-12565, (vol. 124).
Peter E. Maligres et al., "A highly catalytic robust palladium catalyzed cyanation of aryl bromides", Tetrahedron Letters, (1999), 8193-8195, (vol. 40).
Von J.M. Bastian et al., "4H-Benzo[4,5]cyclohepta[1,2-b]thiophene", Helvetica Chimica Acta, (1966), 214-233, (vol. 49).

* cited by examiner

*Primary Examiner* — Nyeemah A Grazier
(74) *Attorney, Agent, or Firm* — Oliff PLC

(57) ABSTRACT

An aminopropylidene derivative having excellent histamine receptor antagonistic action, a compound which is useful as a pharmaceutical composition, especially as an active ingredient, having alleviated side effects in the central nervous system is described. In the aminopropylidene derivative, $R_1$ and $R_2$, which may be identical or different, stand for a hydrogen, a substituted carbonyl, a substituted carbonylalkyl, and acrylic acid, excluding a case where both are hydrogen; $R_3$ and $R_4$, which may be identical or different, stand for hydrogen, an alkyl which may be substituted with phenyl, or the like; A stands for unsubstituted or an oxo; B stands for a carbon or an oxygen; one of X and Y stands for a carbon and the other stands for a sulfur, a broken line part stands for a single bond or a double bond, and a wavy line stands for cis-form and/or trans-form.

22 Claims, No Drawings

AMINOPROPYLIDENE DERIVATIVE

TECHNICAL FIELD

The present invention relates to an aminopropylidene derivative and salt and hydrate thereof that are pharmaceutically acceptable, which are useful as pharmaceutical compositions, particularly active ingredients such as antihistamines.

BACKGROUND ART

Histamines are representative chemical mediators that induce allergic reactions, and the histamines are released from cells such as mast cells and basophils when substances that are causative of allergy are entered into the body. The released histamines are bound to a histamine type 1 receptor (H1 receptor) protein to exhibit pharmacological actions such as hypotension, vascular hyperpermeability, constriction of smooth muscles, vasodilatation, or glandular hypersecretion, and involved in the manifestation of allergic reactions and inflammations. As described above, histamines are related to various diseases of human, and the allergic diseases and inflammations can be prevented or cured by controlling their actions. Agents for controlling histamine release and agents for inhibiting the binding of histamines with receptors (antihistamines) are numerously commercially available, and the agents are used in diseases such as bronchial asthma, allergic rhinitis, pollinosis, urticaria, and atopic dermatitis.

However, antihistamines that are conventionally known to exhibit some undesired side effects such as sedative action, drowsiness, dizziness, and malaise, based on the actions on the central nervous system; and dry mouth, mucosal dryness, and visual impairment, based on the anti-cholinergic actions; therefore, there are some limitations of use such as prohibition of taking antihistamines before driving automobiles, which in turn cause inconvenience in use. For these reasons, antihistamines which are free from such problems and have excellent effects are in demand from the patients and the medical sites. The present inventors have found an aminopropylidene derivative of the present invention having smaller side effects of the central nervous system and potent antihistamine action.

Regarding aminopropyliden derivatives having a thiabenzo azulene backbone, Non-Patent Publication 1 discloses compounds having a thiophene ring or benzene ring with substitution of halogen, methoxy, or dimethylaminosulfonyl. However, the publication only describes that these compounds are synthesized, and does not concretely describe that these compounds have pharmacological actions such as antihistamine actions.

PRIOR ART PUBLICATIONS

Non-Patent Publication(s)

Non-Patent Publication 1: *Helvetica Chimica Acta,* 49, No. 26, (1966), 214-234 (see, pages 220-221, table 3)

SUMMARY OF THE INVENTION

Problems to be Solved by the Invention

An object of the present invention is to provide a pharmaceutical composition that has smaller side effects in the central nervous system, such as drowsiness, and excellent action, particularly a useful compound as an active ingredient such as an antihistamine.

Means to Solve the Problems

As a result of intensive studies on antihistamine compounds having the characteristics mentioned above, the present inventors have found that an aminopropylidene derivative represented by the structural formula (I) given below is a compound useful as a medicament that has excellent antihistamine action and alleviates side effects in the central nervous system, such as drowsiness. The present invention has been perfected thereby.

Effects of the Invention

The aminopropylidene derivative of the present invention has an excellent antagonistic action for histamine receptors and shows low brain transfer even in a cerebral receptor binding test where a mouse is orally administered with the compound, and consequently exhibits an effect of alleviating side effects in the central nervous system, such as drowsiness. Therefore, the aminopropylidene derivative has properties desired for active ingredients of pharmaceutical compositions such as antihistamines, and is highly useful.

MODES FOR CARRYING OUT THE INVENTION

The present invention relates to an aminopropylidene derivative, and salt and hydrate thereof that are pharmaceutically acceptable, that is useful as a medicament such as antihistamines, wherein the aminopropylidene derivative is represented by the following general formula (I):

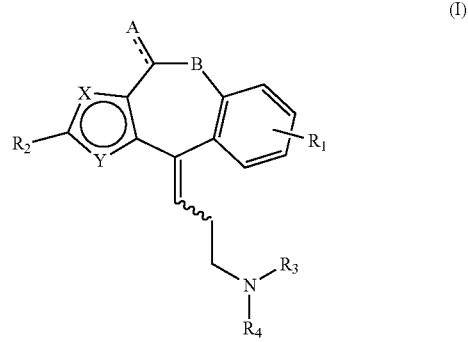

(I)

wherein $R_1$ and $R_2$, which may be identical or different, stand for a hydrogen or a substituent selected from the following (a) to (c) with proviso that a case where both are hydrogen is excluded:
(a) a carbonyl substituted with hydroxy, alkoxy, hydroxyalkylamino,
(b) a carbonylalkyl substituted with hydroxy or alkoxy, and
(c) acrylic acid including an alkyl ester thereof,
$R_3$ and $R_4$, which may be identical or different, stand for a hydrogen, an alkyl which may be substituted with phenyl, or a cycloalkyl, or
$R_3$ and $R_4$, which together form a heterocyclic ring with a nitrogen atom bonded thereto, stand for a pyrrolidino, a piperidino which may be substituted with oxo or piperidino, a piperadinyl substituted with alkyl or phenyl, a morpholino, or a thiomorpholino,
A stands for unsubstituted or an oxo, B stands for a carbon or an oxygen, one of X and Y stands for a carbon and the other stands for a sulfur, a broken line part stands for a single bond or a double bond, and a wavy line stands for cis-form and/or trans-form.

In the above-mentioned general formula (I), the alkyl (including the "alkyl" in the above-mentioned substituents, such as a carbonylalkyl, an alkyl ester of acrylic acid, a hydroxyalkylamino, or an alkylpiperadinyl) stands for a linear or branched alkyl group having 1 to 6 carbon atoms, and the alkyl group is preferably a methyl, an ethyl, a propyl, an isopropyl, a butyl, an isobutyl, a sec-butyl, a t-butyl, a pentyl, an isopentyl, a neopentyl, a t-pentyl, a hexyl, an isohexyl or the like.

The alkoxy stands for a linear or branched alkoxy group having 1 to 6 carbon atoms, and the alkoxy group is preferably a methoxy, an ethoxy, an n-propoxy, an isopropoxy, an n-butoxy, an isobutoxy, a sec-butoxy, a t-butoxy, an n-pentyloxy, an n-hexyloxy, or the like.

The cycloalkyl stands for a cyclic alkyl having 3 to 6 carbon atoms, and the cycloalkyl is preferably a cyclopropyl, a cyclobutyl, a cyclopentyl, or a cyclohexyl.

The halogen stands for a fluorine, a chlorine, a bromine, an iodine, or the like.

Among the compounds of the present invention, preferred compounds are as follows.

Ethyl (E,Z)-3-[4-(3-dimethylaminopropylidene)-9,10-dihydro-4H-3-thiabenzo[f]azulen-2-yl]acrylate hydrochloride [Compound 1]

Ethyl (E,Z)-4-(3-dimethylaminopropylidene)-4,10-dihydro-9-oxa-3-thiabenzo[f]azulene-6-carboxylate hydrochloride [Compound 3]

(E,Z)-4-(3-dimethylaminopropylidene)-4,10-dihydro-9-oxa-3-thiabenzo[f]azulene-6-carboxylic acid [Compound 4]

(E)-[4-(3-Dimethylaminopropylidene)-9,10-dihydro-4H-3-thiabenzo[f]azulen-2-yl]acetic acid hydrochloride [Compound 5]

Ethyl (E,Z)-3-[4-(3-dimethylaminopropylidene)-9,10-dihydro-4H-1-thiabenzo[f]azulen-2-yl]acrylate hydrochloride [Compound 6]

(E,Z)-3-[4-(3-Dimethylaminopropylidene)-9,10-dihydro-4H-1-thiabenzo[f]azulen-2-yl]acrylic acid [Compound 7]

(E,Z)-4-(3-Dimethylaminopropylidene)-9,10-dihydro-4H-3-thiabenzo[f]azulene-2-carboxylic acid [Compound 8]

(E,Z)-4-(3-Dimethylaminopropylidene)-9,10-dihydro-4H-1-thiabenzo[f]azulene-2-carboxylic-(2-hydroxyethyl)amide hydrochloride [Compound 9]

(E,Z)-3-[4-(3-Dimethylaminopropylidene)-9,10-dihydro-4H-3-thiabenzo[f]azulen-2-yl]acrylic acid [Compound 11]

(E)-4-(3-Dimethylaminopropylidene)-9,10-dihydro-4H-3-thiabenzo[f]azulene-2-carboxylic-(2-hydroxyethyl)amide [Compound 12]

Ethyl (E,Z)-3-[4-(3-dimethylaminopropylidene)-4,10-dihydro-9-oxa-3-thiabenzo[f]azulen-6-yl]acrylate hydrochloride [Compound 13]

(E,Z)-3-[4-(3-Dimethylaminopropylidene)-4,10-dihydro-9-oxa-3-thiabenzo[f]azulen-6-yl]acrylic acid [Compound 14]

(E)-[4-(3-Dimethylaminopropylidene)-9,10-dihydro-4H-1-thiabenzo[f]azulen-2-yl]carboxylic acid [Compound 15]

(Z)-[4-(3-Dimethylaminopropylidene)-9,10-dihydro-4H-1-thiabenzo[f]azulen-2-yl]carboxylic acid [Compound 16]

(E)-[4-(3-Dimethylaminopropylidene)-9,10-dihydro-4H-1-thiabenzo[f]azulen-2-yl]acetic acid hydrochloride [Compound 17]

(Z)-[4-(3-Dimethylaminopropylidene)-9,10-dihydro-4H-1-thiabenzo[f]azulen-2-yl]acetic acid hydrochloride [Compound 18]

(E)-[4-(3-Dimethylaminopropylidene)-4,10-dihydro-9-oxa-3-thiabenzo[f]azulen-6-yl]acetic acid [Compound 19]

(Z)-[4-(3-Dimethylaminopropylidene)-4,10-dihydro-9-oxa-3-thiabenzo[f]azulen-6-yl]acetic acid [Compound 20]

Ethyl (E,Z)-2-[4-(3-dimethylaminopropylidene)-4,10-dihydro-9-oxa-3-thiabenzo[f]azulen-6-yl]-2-methylpropionate hydrochloride [Compound 21]

(E,Z)-2-[4-(3-Dimethylaminopropylidene)-4,10-dihydro-9-oxa-3-thiabenzo[f]azulen-6-yl]-2-methylpropionic acid [Compound 22]

(E,Z)-2-[4-(3-Dimethylaminopropylidene)-9,10-dihydro-4H-1-thiabenzo[f]azulen-2-yl]-2-methylpropionic acid [Compound 23]

Ethyl (E,Z)-2-[4-(3-dimethylaminopropylidene)-10-oxo-9,10-dihydro-4H-1-thiabenzo[f]azulen-2-yl]-2-methylpropionate hydrochloride [Compound 24]

(E)-{2-Methyl-2-[4-(3-methylaminopropylidene)-4,10-dihydro-9-oxa-3-thiabenzo [f]azulen-6-yl]}propionic acid [Compound 25]

(E)-{4-[3-(Pyrrolidin-1-yl)propylidene]-4,10-dihydro-9-oxa-3-thiabenzo[f]azulen-6-yl}acetic acid [Compound 26]

(Z)-{4-[3-(Pyrrolidin-1-yl)propylidene]-4,10-dihydro-9-oxa-3-thiabenzo[f]azulen-6-yl}acetic acid [Compound 27]

(Z)-[4-(3-Dimethylaminopropylidene)-4,10-dihydro-9-oxa-1-thiabenzo[f]azulen-6-yl]acetic acid [Compound 28]

(E)-[4-(3-Dimethylaminopropylidene)-4,10-dihydro-9-oxa-1-thiabenzo[f]azulen-6-yl]acetic acid [Compound 29]

(E)-[4-(3-Ethylmethylaminopropylidene)-4,10-dihydro-9-oxa-3-thiabenzo[f]azulen-6-yl]acetic acid [Compound 30]

(Z)-[4-(3-Ethylmethylaminopropylidene)-4,10-dihydro-9-oxa-3-thiabenzo[f]azulen-6-yl]acetic acid [Compound 31]

(E)-{4-[3-(Morpholin-4-yl)propylidene]-4,10-dihydro-9-oxa-3-thiabenzo[f]azulen-6-yl}acetic acid [Compound 32]

(Z)-{4-[3-(Morpholin-4-yl)propylidene]-4,10-dihydro-9-oxa-3-thiabenzo[f]azulen-6-yl}acetic acid [Compound 33]

(E)-{4-[3-(Piperidin-1-propylidene]-4,10-dihydro-9-oxa-3-thiabenzo[f]azulen-6-yl}acetic acid [Compound 34]

(Z)-{4-[3-(Piperidin-1-yl)propylidene]-4,10-dihydro-9-oxa-3-thiabenzo[f]azulen-6-yl}acetic acid [Compound 35]

(E)-4-{4-[3-(Pyrrolidin-1-yl)propylidene]-4,10-dihydro-9-oxa-3-thiabenzo[f]azulen-6-yl}butyric acid [Compound 36]

(Z)-4-{4-[3-(Pyrrolidin-1-yl)propylidene]-4,10-dihydro-9-oxa-3-thiabenzo[f]azulen-6-yl}butyric acid [Compound 37]

(E)-[4-(3-Ethylaminopropylidene)-4,10-dihydro-9-oxa-3-thiabenzo[f]azulen-6-yl]acetic acid [Compound 38]

(Z)-[4-(3-Ethylaminopropylidene)-4,10-dihydro-9-oxa-3-thiabenzo[f]azulen-6-yl]acetic acid [Compound 39]

(E)-[4-(3-Benzylmethylaminopropylidene)-4,10-dihydro-9-oxa-3-thiabenzo[f]azulen-6-yl]acetic acid [Compound 40]

(Z)-[4-(3-Benzylmethylaminopropylidene)-4,10-dihydro-9-oxa-3-thiabenzo[f]azulen-6-yl]acetic acid [Compound 41]

(E)-[4-(3-Benzylaminopropylidene)-4,10-dihydro-9-oxa-3-thiabenzo[f]azulen-6-yl]acetic acid [Compound 42]

(Z)-[4-(3-Benzylaminopropylidene)-4,10-dihydro-9-oxa-3-thiabenzo[f]azulen-6-yl]acetic acid [Compound 43]

(E)-[4-(3-Cyclopentylaminopropylidene)-4,10-dihydro-9-oxa-3-thiabenzo[f]azulen-6-yl]acetic acid [Compound 44]

(Z)-[4-(3-Cyclopentylaminopropylidene)-4,10-dihydro-9-oxa-3-thiabenzo[f]azulen-6-yl]acetic acid [Compound 45]

(E)-[4-(3-Isopropylaminopropylidene)-4,10-dihydro-9-oxa-3-thiabenzo[f]azulen-6-yl]acetic acid [Compound 46]

(Z)-[4-(3-Isopropylaminopropylidene)-4,10-dihydro-9-oxa-3-thiabenzo[f]azulen-6-yl]acetic acid [Compound 47]

(E)-3-[4-(3-Dimethylaminopropylidene)-4,10-dihydro-9-oxa-3-thiabenzo[f]azulen-6-yl]propionic acid [Compound 48]

(Z)-3-[4-(3-Dimethylaminopropylidene)-4,10-dihydro-9-oxa-3-thiabenzo[f]azulen-6-yl]propionic acid [Compound 49]

(E)-{4-[3-(4-Methylpiperadin-1-yl)propylidene]-4,10-dihydro-9-oxa-3-thiabenzo[f]azulen-6-yl}acetic acid [Compound 50]

(Z)-{4-[3-(4-Methylpiperadin-1-yl)propylidene]-4,10-dihydro-9-oxa-3-thiabenzo[f]azulen-6-yl}acetic acid [Compound 51]

(E)-3-{4-[3-(Pyrrolidin-1-yl)propylidene]-4,10-dihydro-9-oxa-3-thiabenzo[f]azulen-6-yl}propionic acid [Compound 52]

(Z)-3-{4-[3-(Pyrrolidin-1-yl)propylidene]-4,10-dihydro-9-oxa-3-thiabenzo[f]azulen-6-yl}propionic acid [Compound 53]

(E)-{4-[3-(4-Phenylpiperadin-1-yl)propylidene]-4,10-dihydro-9-oxa-3-thiabenzo[f]azulen-6-yl}acetic acid [Compound 54]

(Z)-{4-[3-(4-Phenylpiperadin-1-yl)propylidene]-4,10-dihydro-9-oxa-3-thiabenzo[f]azulen-6-yl}acetic acid [Compound 55]

(E)-3-[4-(3-Dimethylaminopropylidene)-4,10-dihydro-9-oxa-1-thiabenzo[f]azulen-6-yl]propionic acid hydrochloride [Compound 56]

(Z)-3-[4-(3-Dimethylaminopropylidene)-4,10-dihydro-9-oxa-1-thiabenzo[f]azulen-6-yl]propionic acid hydrochloride [Compound 57]

(E)-3-{4-[3-(Pyrrolidin-1-yl)propylidene]-4,10-dihydro-9-oxa-1-thiabenzo[f]azulen-6-yl}propionic acid [Compound 58]

(Z)-3-{4-[3-(Pyrrolidin-1-yl)propylidene]-4,10-dihydro-9-oxa-1-thiabenzo[f]azulen-6-yl}propionic acid [Compound 59]

(E)-4-[4-(3-Dimethylaminopropylidene)-4,10-dihydro-9-oxa-3-thiabenzo[f]azulen-6-yl]butyric acid [Compound 60]

(Z)-4-[4-(3-Dimethylaminopropylidene)-4,10-dihydro-9-oxa-3-thiabenzo[f]azulen-6-yl]butyric acid [Compound 61]

(E)-{4-[3-(4-Oxopiperidin-1-yl)propylidene]-4,10-dihydro-9-oxa-3-thiabenzo[f]azulen-6-yl}acetic acid [Compound 62]

(Z)-{4-[3-(4-Oxopiperidin-1-yl)propylidene]-4,10-dihydro-9-oxa-3-thiabenzo[f]azulen-6-yl}acetic acid [Compound 63]

(E)-[4-(3-Dimethylaminopropylidene)-9,10-dihydro-4H-3-thiabenzo[f]azulen-6-yl]acetic acid [Compound 64]

(Z)-[4-(3-Dimethylaminopropylidene)-9,10-dihydro-4H-3-thiabenzo[f]azulen-6-yl]acetic acid hydrochloride [Compound 65]

(E)-{4-[3-([1,4']Bipiperidin-1'-yl)propylidene]-4,10-dihydro-9-oxa-3-thiabenzo[f]azulen-6-yl}acetic acid diformate [Compound 66]

(Z)-{4-[3-([1,4']Bipiperidin-1'-yl)propylidene]-4,10-dihydro-9-oxa-3-thiabenzo[f]azulen-6-yl}acetic acid diformate [Compound 67]

(E,Z)-{4-[3-(Thiomorpholin-4-yl)propylidene]-4,10-dihydro-9-oxa-3-thiabenzo[f]azulen-6-yl}acetic acid [Compound 68]

(E,Z)-2-Methyl-2-{4-[3-(pyrrolidin-1-yl)propylidene]-9,10-dihydro-4H-1-thiabenzo[f]azulen-2-yl}propionic acid [Compound 69]

(E)-{4-[3-(Pyrrolidin-1-yl)propylidene]-4,10-dihydro-9-oxa-3-thiabenzo[f]azulen-6-yl}acetic acid hydrochloride [Compound 70]

(Z)-{4-[3-(Pyrrolidin-1-yl)propylidene]-4,10-dihydro-9-oxa-3-thiabenzo[f]azulen-6-yl}acetic acid hydrochloride [Compound 71]

Among the above compounds of the present invention, more preferred compounds include compounds listed in Tables 9 and 10 set forth later. Further, compounds listed in Table 12 having excellent antihistamine actions and low brain transfer are especially preferred.

A general method for producing the compound of the present invention will be given hereinbelow. The compound of the present invention represented by the above-mentioned general formula (I) can be produced according to the method described below. Here, it is obvious for one of ordinary skill in the art that the exact methods usable in the production of specified compounds can vary depending upon their chemical structures.

Of the above-mentioned compounds of the present invention represented by the general formula (I), a 4-(aminopropylidene)-9,10-dihydro-4H-1-thiabenzo[f]azulene compound can be produced in accordance with methods described in *Helvetica Chimica Acta,* 49, Fasc. Emile Cherbuliez, No. 26, 214-233 (1966) or *Collect. Czech. Chem. Commun.* 59, 667-674 (1994), a 4-(aminopropylidene)-9,10-dihydro-4H-3-thiabenzo[f]azulene compound can be produced in accordance with methods described in *Helvetica Chimica Acta,* 54, Fasc. 1, 277-282 (1971), a 4-(aminopropylidene)-4H-1-thiabenzo[f]azulene compound and a 4-(aminopropylidene)-4H-3-thiabenzo[f]azulene compound can be produced in accordance with methods described in *Helvetica Chimica Acta,* 49, Fasc. Emile Cherbuliez No. 26, 214-233 (1966), a 4-(aminopropydene)-4,10-dihydro-9-oxa-1-thiabenzo[f]azulene compound and a 4-(aminopropylidene)-4,10-dihydro-9-oxa-3-thiabenzo[f]azulene compound can be produced in accordance with methods described in Japanese Patent Laid-Open No. Sho 63-10784 or WO 2005/003131, and a 4-(aminopropylidene)-10-oxo-9,10-dihydro-4H-1-thiabenzo[f]azulene compound can be produced in accordance with methods described in *Helvetica Chimica Acta,* 59, Fasc. 3, 866-877 (1976). Here, the introduction of substituents is accomplished by selecting starting raw materials previously having any substituents at a position corresponding thereto.

The compound of the general formula (I) can be produced by Wittig reaction, Wittig-Horner reaction, McMurry reaction of a compound of general formula (II). For example, in the case when Wittig reaction is used, the production can be carried out in accordance to the method described in *J. Org. Chem.* 44, 22, 3760-3765 (1979), *J. Med. Chem.* 35, 2074-2084 (1992), or the like. In the other words, the compound of the general formula (I) can be produced by reacting the compound of the general formula (II) with a corresponding 3-aminopropylphosphonium salt or the like, in the presence of a base such as n-butyllithium or potassium butoxide, in a non-aqueous solvent such as THF (tetrahydrofuran), toluene, diethyl ether, or CPME (cyclopentyl methyl ether), at a suitable temperature preferably between 0° C. and a boiling point of the solvent.

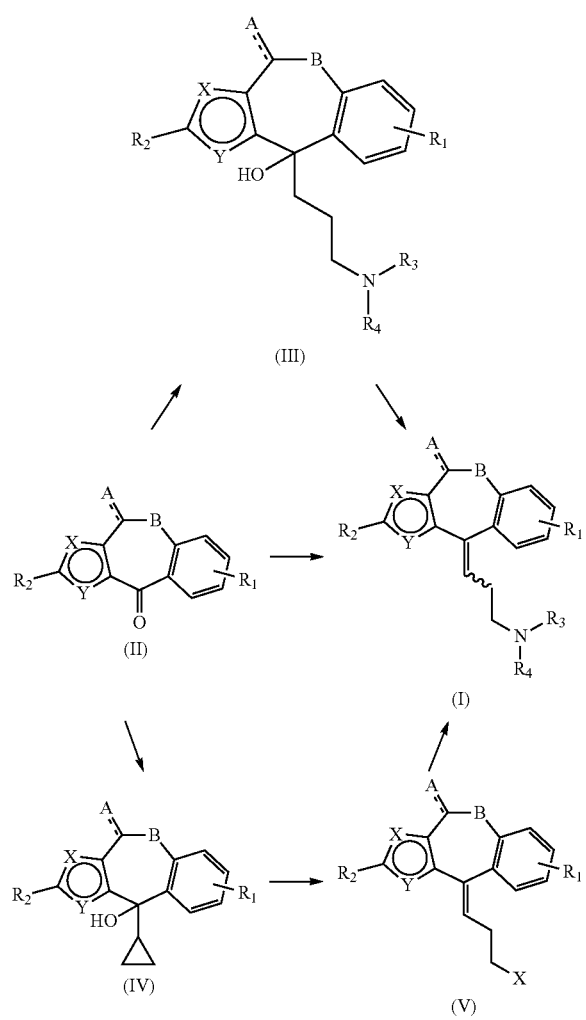

In addition, the compound of the general formula (II) can be converted to the compound of the general formula (I) by subjecting a compound represented by the general formula (III) formed after a Grignard reaction to a dehydration reaction. This production method can be carried out in accordance with the method described in *Helvetica Chimica Acta,* 54, Fasc. 1, 277-283 (1971). For example, a Grignard reaction is carried out by treating a compound of the general formula (II) with a Grignard reagent, such as a 3-aminopropyl magnesium halide, corresponding thereto, in a non-aqueous solvent such as THF, toluene, diethyl ether or CPME, at a suitable temperature from a melting point to a boiling point of the solvent. The subsequent dehydration reaction can be carried out with hydrochloric acid, trifluoroacetic acid, thionyl chloride or the like, in the absence of a solvent or in a suitable solvent such as water, ethanol, or dichloromethane, at an optimal reaction temperature from a melting point to a boiling point of the solvent.

Further, as an alternative method, a method described in *Collect. Czech. Chem. Commum.* 59, 667-674 (1994) can be used. In the other words, the compound of the general formula (II) is treated with a Grignard reagent prepared from magnesium and bromocyclopropane or the like, in a non-aqueous solvent such as THF, toluene or CPME at a suitable temperature between a melting point and a boiling point of the solvent to give a compound represented by the general formula (IV).

Thereafter, the resulting compound is subjected to, a halogenation reaction with hydrobromic acid, trimethylsilane bromide, thionyl chloride or the like, in a suitable solvent such as water, acetic acid, dichloromethane, chloroform or 1,4-dioxane, at a suitable temperature between 0° C. and a boiling point of the solvent, thereby converting the compound into a compound represented by the general formula (V). Subsequently, the resulting halogenated product can be treated with a corresponding amine compound in a solvent such as acetone, methanol, ethanol, THF, 1,4-dioxane or acetonitrile at a suitable temperature preferably between room temperature and a boiling point of the solvent, whereby the compound (I) can be produced. In this amination reaction, potassium carbonate, sodium hydroxide, triethylamine or the like can be properly used as a base, as occasion demands.

The compound of the formula (II) can be produced in accordance with the method described in Japanese Patent Laid-Open No. Sho-49-69677, *Helvetica Chimica Acta,* 54, Fasc. 1, 214-233 (1996), *Helvetica Chimica Acta,* 54, Fasc. 1, 277-282 (1971), WO 2005/003131, Japanese Patent Application No. 2008-019121 and the like.

The formation of the functional groups on the aromatic ring can be accomplished by subjecting a compound of the general formula (I), a compound of the general formula (II), or a compound of the general formula (III) or (IV) synthesized using a Grignard reagent mentioned above to a lithioformation reaction with an alkyllithium reagent, a Friedel-Crafts acylation reaction, a Vilsmeier formylation reaction, or the like. Further, a compound having a brominated aromatic ring is selected as a raw material and subjected to a carbonylation reaction, a Heck reaction, a cyanation reaction, a formylation reaction, an Ullmann reaction, a Suzuki coupling reaction, or the like, with or without a transition metal catalyst such as palladium, whereby the aromatic ring can be converted to have a desired functional group. In this kind of a reaction, a method described in *J. Am. Chem. Soc.,* 124, 12557-12565 (2002), *Tetrahedron Lett.,* 40, 8193-8195 (1991), or the like can be also used.

For example, the alkylation reaction can be formed by treating a compound having a brominated aromatic ring using an ester derivative, such as ethyl acetate, t-butyl acetate, or ethyl isobutyrate, a base, such as potassium butoxide, potassium hydride, LiHMDS (lithium hexamethyl disilazide), or LiNCy$_2$ (lithium dicyclohexylamide), and a ligand, such as DPPF (1,1'-bis(diphenylphosphino)ferrocene), PPh$_3$ (triphenylphosphine), P (o-Tol)$_3$(tris(2-methylphenyl)phosphine), P(t-Bu)$_3$ (tri-t-butylphosphine), or N,N'-(2,6-diisopropylphenyl)dihydroimidazolium chloride, in the presence of a transition metal catalyst such as Pd(dba)$_2$ (palladium(0) bis (dibenzylidene acetone)), Pd$_2$(dba)$_3$ (dipalladium(0) tris (dibenzylidene acetone)), Pd(OAc)$_2$ (palladium(II) acetate), or Pd(PPh$_3$)$_4$ (palladium(0) tetrakis(triphenylphosphine)). This reaction can be carried out in the solvent such as toluene, benzene, pentane, cyclohexane or mixture thereof, at a suitable temperature preferably between a room temperature and a boiling point of the solvent.

The above-mentioned compound of the general formula (I) also embraces a cis-trans isomeric mixture thereof, and these isomers can be separated by liquid chromatography, or a preferential crystallization method with or without a suitable counterion. For example, in a case where a high-performance liquid chromatography is used, the separation is accomplished by using a mixture suitably formulated with an organic solvent such as methanol or acetonitrile and an aqueous solution to which formic acid or trifluoroacetic acid are added, as occasion demands, as an eluent.

The compound represented by the general formula (I) mentioned above includes, in a case where a pharmaceutically acceptable salt thereof is present, various kinds of salts thereof, and include, for example, addition salts with an acid such as hydrochloric acid, oxalic acid, fumaric acid, p-toluenesulfonic acid, maleic acid, succinic acid, acetic acid, citric acid, tartaric acid, carbonic acid, nitric acid or formic acid. The salts of carboxyl group of the compounds can also include suitable alkali metal salt of sodium, potassium, calcium and the like. These salts can be produced from each compound in a free form, or converted reversibly, in accordance with a known method. In addition, in a case where the compounds are present in the state of a steric isomer such as a cis-trans isomer, an optical isomer or a coordination isomer, or a hydrate or a metal complex compound, the present invention embraces any of steric isomers, hydrates, and complex compounds.

The compound of the present invention can be combined with a suitable pharmaceutical carrier or diluent to form a medicament. Also, the compound can be produced into preparations by any ordinary methods, and the compounds can be produced into formulations as an orally administered agent such as a tablet, a capsule, a fine powder, or a liquid, or as a parenterally administered agent for subcutaneous administration, intramuscular administration, intrarectal administration, or intranasal administration. In the prescription, the compound of the present invention may be used in the form of a pharmaceutically acceptable salt thereof, and the compounds can be used alone or in a proper combination, and further, a blending agent with another pharmaceutically active ingredient.

The orally administered preparation can be used directly, or in a proper combination with a suitable additive, for example, a conventional excipient such as lactose, mannitol, corn starch, or potato starch, together with a binder such as a crystalline cellulose, a cellulose derivative, gum arabic, corn starch, or gelatin, a disintegrant such as corn starch, potato starch, carboxymethyl cellulose potassium, a lubricant such as talc or magnesium stearate, and other additive such as a filler, a wetting agent, a buffer, a preservative, or perfume, and the like to produce a tablet, a powder, a granule, or a capsule.

In addition, the compound can be produced into preparations in a dosage form other than above that is optimal for the treatment depending upon the kinds of the disease and the patients, including, for example, externally administered agents, such as injections, suppositories, inhalants, aerosols, syrups, instillations, and ointments, and the like.

The desired dose for the compound of the present invention may vary depending upon the subject to be administered, the dose form, the administration method, the administration time period, and the like. In order to obtain a desired effect, the compound of the present invention can be generally orally administered in an amount of from 0.5 to 1000 mg, and preferably from 1 to 500, for adult, at once or in several divided administrations per day. In the case of the parenteral administration (for example, an injection), the daily dose is preferably from one-third to one-tenth the dose level for each of the doses mentioned above.

EXAMPLES

Next, the present invention will be specifically described hereinbelow by the Examples, without intending to limit the scope of the present invention thereto.

A melting point was determined by placing a sample in a glass capillary tube, and using Yamato Scientific, Model MP-21, a melting point measuring instrument. No compensation of the thermometer was made. The MS spectrum was measured with POLARIS Q (Thermo Quest). $^1$H-NMR was measured with a nuclear magnetic resonance analyzer Model ARX500 (Bruker), in which chemical shift when measured in a deuterated organic solvent was expressed in ppm, using an internal standard TMS ($\delta$=0 ppm) as a standard. Also, when measured in deuterated water, a peak ascribed to water at 4.67 ppm was used as an internal standard. Silica gel column chromatography was performed using silica gel PSQ 100B or NH-DM1020 for chromatography (FUJI SILYSIA CHEMICAL LTD.). Thin-layer chromatography was performed using silica gel F254 (Merck, No. 5715) or TLC Plate NH (FUJI SILYSIA CHEMICAL LTD.), and detection was made using a UV lamp and a 5% phosphomolybdic acid-ethanol color development reagent. The separation of geometric isomers was performed by high-performance liquid chromatography, using 880-PU (Nippon Bunko) as a liquid-conveying pump, 875-UV (Nippon Bunko) as a detector, and STR PREP-ODS (20 mm I.D.×250 mm) (Shinwa Kako) as a preparative column Example 1

Production of Ethyl 3-(4-Oxo-9,10-dihydro-4H-3-thiabenzo[f]azulen-2-yl)acrylate

Triethylamine (34 mL), ethyl acrylate (27.5 mL), palladium acetate (0.4 g), and P(o-Tol)$_3$ (1.5 g) were added to a DMF (50 mL) solution of 2-bromo-9,10-dihydro-3-thiabenzo[f]azulen-4-one (7.00 g), and the mixture was stirred overnight at 80° C. in an argon atmosphere. An aqueous saturated ammonium chloride solution was added to the reaction mixture, the mixture was extracted with ethyl acetate, and the organic layer was then washed with an aqueous saturated sodium chloride solution, and dried over anhydrous sodium sulfate. The solvent was distilled off under a reduced pressure, and the residue obtained was purified by silica gel column chromatography (chloroform-methanol=9:1), to give 6.39 g (85%) of the captioned compound as an amorphous solid.

$^1$H-NMR(DMSO-d$_6$) $\delta$: 1.26 (t, J=7.1 Hz, 3H), 3.10-3.19 (m, 4H), 4.19 (q, J=7.1 Hz, 2H), 6.55 (d, J=16.1 Hz, 1H), 7.40-7.44 (m, 2H), 7.55-7.59 (m, 2H), 7.80-7.82 (m, 1H), 8.59 (s, 1H).

Example 2

Production of Ethyl (E,Z)-3-[4-(3-Dimethylaminopropylidene)-9,10-dihydro-4H-3-thiabenzo[f]azulen-2-yl]acrylate Hydrochloride [Compound 1]

A 1.6 mol/L n-butyllithium-hexane solution (42 mL) was added to a THF (100 mL) solution of dimethylaminopropyltriphenylphosphonium hydrobromide (23.5 g) under ice-cooling, and the mixed solution was stirred at room temperature for 1 hour. A THF (100 mL) solution of the compound obtained in Example 1 (6.11 g) was added to this solution, and the mixture was further stirred overnight. The solvent was distilled off under a reduced pressure, an aqueous saturated ammonium chloride solution was added to the residue, and the mixture was extracted with ethyl acetate. The organic layer was washed with an aqueous saturated sodium chloride solution, and then dried over anhydrous sodium sulfate, and the solvent was distilled off under a reduced pressure. The residue was purified by silica gel column chromatography (chloroform-methanol=9:1), the purified product obtained was dissolved in 1,4-dioxane (20 mL), a 4 mol/L hydrogen chloride-dioxane solution (1.1 mL) was thereto, and the mixture was stirred at room temperature for 1 hour. The solvents were distilled off under a reduced pressure, and the precipitated crystals were filtered off and dried, to give 0.51 g (6%) of the captioned compound as a mixture of E-form and Z-form.

Example 3

Production of t-Butyl (E,Z)-[4-(3-Dimethylaminopropylidene)-4,10-dihydro-9-oxa-3-thiabenzo[f]azulen-6-yl]acetate A 1.6 mol/L n-butyllithium-hexane solution (14 mL) was added dropwise to hexamethyldisilazane (3.53 g) in an argon atmosphere under ice-cooling. t-Butyl acetate (1.2 mL) was added dropwise to the solution, and stirred for 30 minutes. Pd(dba)$_2$ (0.30 g), N,N'-(2,6-diisopropylphenyl)dihydroimidazolinium chloride (0.22 g), and (E,Z)-[3-(6-bromo-10H-9-oxo-3-thiabenzo[f]azulen-4-ylidene)propyl]dimethylamine (2.01 g) were added, and the mixture was heated to room temperature and stirred overnight. An aqueous saturated amminum chloride solution was added to the reaction mixture, and the mixture was extracted with ethyl acetate. The organic layer was washed with an aqueous saturated sodium chloride solution, and then dried over anhydrous sodium sulfate. The solvent was distilled off under a reduced pressure, and the residue obtained was purified by silica gel column chromatography (hexane-ethyl acetate=19:1), to give 0.80 g (36%) of the captioned compound as an oily product of a mixture of E-form and Z-form.
MS (EI):m/z 400 [M$^+$+1]. $^1$H-NMR (DMSO-d$_6$) δ: 1.35-1.42 (m, 9H), 2.07-2.66 (m, 10H), 3.51-3.55 (m, 2H), 5.05-5.12 (m, 2H), 5.84-6.06 (m, 1H), 6.77-7.53 (m, 5H).

Example 4

Production of (E,Z)-[4-(3-Dimethylaminopropylidene)-4,10-dihydro-9-oxa-3-thiabenzo[f]azulen-6-yl]acetic Acid Trifluoroacetic acid (2.0 mL) was gradually added to the compound obtained in Example 3 (1.53 g), and the mixture was stirred at room temperature for 2 hours. Trifluoroacetic acid was distilled off under a reduced pressure, a 5% aqueous potassium carbonate solution was added to the residue, a pH of the solution was then adjusted to 7 with a diluted hydrochloric acid, and the solution was extracted with chloroform. The organic layer was washed with an aqueous saturated sodium chloride solution, and then dried over anhydrous sodium sulfate. The solvent was distilled off under a reduced pressure, to give 1.20 g (91%) of the captioned compound as an oily product of a mixture of E-form and Z-form.

Example 5

Production of (E)-[4-(3-Dimethylaminopropylidene)-4,10-dihydro-9-oxa-3-thiabenzo[f]azulen-6-yl]acetic Acid [Compound 19] and (Z)-[4-(3-Dimethylaminopropylidene)-4,10-dihydro-9-oxa-3-thiabenzo[f]azulen-6-yl]acetic Acid [Compound 20]

The compound obtained in Example 4 (1.20 g) was dissolved in 30 mL of a 0.2% aqueous formic acid solution/methanol mixed solution, and a sample solution filtered with a 0.45 μm membrane filter was separated and purified by high-performance liquid chromatography (eluent: a mixed solution of 0.2% formic acid solution/methanol (3:2)). The flow rate was 6.5 mL/minute, and the measurement wavelength was 254 nm. The compound 19 was eluted between 20 minutes and 24 minutes, and the compound 20 was eluted between 15 minutes and 18 minutes. The solvents of each of the collected eluates were distilled off under a reduced pressure, and the precipitated white crystals were filtered off and dried, to give 00.0.53 g (44%) and 0.28 g (23%) of the compound 19 and the compound 20, respectively.

Example 6

Production of Methyl (4-Cyclopropyl-4-hydroxy-4,10-dihydro-9-oxa-3-thiabenzo[f]azulen-6-yl)acetate An anhydrous THF (50 mL) solution of bromocyclopropane (8.3 mL) was added dropwise to a metal magnesium (2.5 g), while heating. After the termination of dropwise addition, an anhydrous THF (20 mL) was added thereto, and the mixture was refluxed under heating for an additional 2 hours. Thereafter, the reaction mixture was allowed to air-cool, and this solution was added dropwise to an anhydrous THF (30 mL) solution of methyl (4-oxo-4,10-dihydro-9-oxa-3-thiabenzo[f]azulen-6-yl)acetate (10.0 g) previously chilled in an ice bath. After stirring the mixture for 30 minutes, an aqueous saturated ammonium chloride solution was added to the reaction mixture, and the mixture was extracted with ethyl acetate. The organic layer was washed with an aqueous saturated sodium chloride solution, and thereafter dried over anhydrous sodium sulfate. The solvents were distilled off under a reduced pressure, and the residue obtained was purified by silica gel column chromatography (hexane-ethyl acetate=5:1), to give 9.0 g (79%) of the captioned compound as an oily product.
$^1$H-NMR (DMSO-d$_6$) δ:0.16-0.18 (m, 1H), 0.29-0.31 (m, 1H), 0.44-0.47 (m, 1H), 0.60-0.62 (m, 1H), 1.74-1.78 (m, 1H), 3.60-3.65 (m, 5H), 4.78 (d, J=15.4 Hz, 1H), 5.36 (d, J=15.4 Hz, 1H), 6.10 (s, 1H), 6.72-6.73 (m, 1H), 7.07-7.51 (m, 4H).

Example 7

Production of Methyl (E,Z)-[4-(3-Bromopropylidene)-4,10-dihydro-9-oxa-3-thiabenzo[f]azulen-6-yl)acetate A dichloromethane (20 mL) solution of trimethylsilane bromide (3.6 mL) was added dropwise to a dichloromethane (100 mL) solution of the compound obtained in Example 6 (9.0 g) at room temperature to carry out a bromination reaction. After stirring the mixture for 1 hour, an aqueous saturated sodium hydrogencarbonate was added thereto, and the organic layer was allowed to separate. The organic layer was washed with an aqueous saturated sodium chloride solution, and thereafter dried over anhydrous sodium sulfate. The solvents were distilled off under a reduced pressure, and thereafter the residue obtained was purified by silica gel column chromatography (hexane-ethyl acetate=9:1), to give 9.3 g (87%) of the captioned compound as an oily product of a mixture of E-form and Z-form.
$^1$H-NMR (DMSO-d$_6$) δ: 2.76-3.10 (m, 2H), 3.60-3.79 (m, 7H), 5.06-5.14 (m, 2H), 5.83-6.06 (m, 1H), 6.79-7.56 (m, 5H).

Example 8

Production of Methyl (E,Z)-{4-[3-(Pyrrolidin-1-yl)propylidene]-4,10-dihydro-9-oxa-3-thiabenzo[f]azulen-6-yl}acetate Pyrrolidine (0.4 mL), sodium carbonate (0.7 g), and potassium iodide (0.9 g) was added to a THF (20 mL) solution of the compound obtained in Example 7 (1.00 g), and the mixture was refluxed under heating overnight. After allowing the mixture to air-cool, an aqueous saturated ammonium chloride solution was added thereto, and the mixture was extracted with ethyl acetate. The organic layer was washed with an aqueous saturated sodium chloride solution, and thereafter dried over anhydrous sodium sulfate. The solvents were distilled off under a reduced pressure, and thereafter the residue obtained was purified by silica gel column chromatography (hexane-ethyl acetate=5:1), to give 0.50 g (51%) of the captioned compound as an oily product of a mixture of E-form and Z-form.
MS (EI): m/z 383 [M$^+$]. $^1$H-NMR (DMSO-d$_6$) δ: 1.63-1.67 (m, 4H), 2.35-2.58 (m, 8H), 3.60-3.69 (m, 5H), 5.05-5.12 (m, 2H), 5.80-6.09 (m, 1H), 6.78-7.53 (m, 5H).

Example 9

Production of (E,Z)-{4-[3-(Pyrrolidin-1-yl)propylidene]-4,10-dihydro-9-oxa-3-thiabenzo[f]azulen-6-yl}acetic acid A 1 mol/L sodium hydroxide (22 mL) was added to an ethanol (30 mL) solution of the compound obtained in Example 8 (2.80 g), and the mixture was stirred at room temperature for 2 hours. The solvent was distilled off, water was then added to the residue, and the aqueous solution was adjusted to a pH of 7 with a diluted hydrochloric acid, and the mixture was extracted with chloroform. The organic layer was washed with an aqueous saturated sodium chloride solution, and thereafter dried over anhydrous sodium sulfate. The solvents were distilled off under a reduced pressure, and an oily product obtained was formed into a solid from diethyl ether, to give 2.21 g (82%) of the captioned compound as crystals of a mixture of E-form and Z-form.

Example 10

Production of (E)-{4-[3-(Pyrrolidin-1-yl)propylidene]-4,10-dihydro-9-oxa-3-thiabenzo[f]azulen-6-yl}acetic acid [Compound 26] and (Z)-{4-[3-(Pyrrolidin-1-yl)propylidene]-4,10-dihydro-9-oxa-3-thiabenzo[f]azulen-6-yl}acetic acid [Compound 27]

The same procedures as in Example 5 were carried out to perform separation and purification using the mixture of E-form and Z-form obtained in Example 9 (1.99 g), to give 1.09 g (55%) and 0.31 g (16%) of the compound 26 and the compound 27, respectively, as white crystals.

Example 11

Production of (E,Z)-[3-(6-Bromo-10H-9-oxa-3-thiabenzo[f]azulen-4-ylidene)-propyl]dimethylamine Hydrochloride [Compound 2]

The same procedures as in Examples 6 and 7 were carried out, in this order, using 6-bromo-10H-9-oxa-3-thiabenzo[f]azulen-4-one (5.10 g), to give a compound, and the same procedures as in Example 8 were carried out using the compound obtained and an aqueous 50% dimethylamine solution, to give 3.62 g (58%) of [3-(6-bromo-10H-9-oxa-3-thiabenzo[f]azulen-4-ylidene)propyl]dimethylamine as an oily product of a mixture of E-form and Z-form. The resulting isomeric mixture (1.0 g) was dissolved in 1,4-dioxane (10 mL), a 4 mol/L hydrogen chloride-dioxane solution (3.0 mL) was added to the solution, and the mixture was stirred at room temperature for 1 hour. The solvents were distilled off under a reduced pressure, and thereafter the precipitated crystals were filtered off and dried, to give 0.85 g (77%) of the captioned compound, which is a hydrochloride of a mixture of E-form and Z-form.

Example 12

Production of (E,Z)-[6-Cyano-4-(3-dimethylaminopropylidene)-4,10-dihydro-9-oxa-3-thiabenzo[f]azulene]

Zinc cyanide (2.27 g), Pd$_2$(dba)$_3$ (1.14 g), and DPPF (3.47 g) were added to a DMF (150 mL) solution of the compound 2 (11.6 g), and the mixture was stirred overnight at 120° C. in an argon atmosphere. After allowing the mixture to air-cool, water was added to the reaction mixture, insoluble substances were filtered off, and the filtrate was extracted with ethyl acetate. The organic layer was washed with an aqueous saturated sodium chloride solution, and thereafter dried over anhydrous sodium sulfate. The solvents were distilled off under a reduced pressure, and thereafter the residue obtained was purified by silica gel column chromatography (hexane-ethyl acetate=9:1), to give 1.70 g (17%) of the captioned compound as an oily product of a mixture of E-form and Z-form.
MS(EI): m/z 311[M$^+$+1]. $^1$H-NMR(DMSO-d$_6$) δ: 2.09-2.13 (m, 6H), 2.31-2.58 (m, 4H), 5.16-5.23 (m, 2H), 6.13-6.16 (m, 1H), 6.81-7.96 (m, 5H).

Example 13

Production of (E,Z)-4-(3-Dimethylaminopropylidene)-4,10-dihydro-9-oxa-3-thiabenzo[f]azulene-6-carboxylic acid [Compound 4]

A 1 mol/L sodium hydroxide (27 mL) was added to an ethanol (25 mL) solution of the compound obtained in Example 12 (1.70 g), and the mixture was refluxed under heating for 6 hours. Subsequently, the reaction mixture was subjected to the same treatments as in Example 9, to give 1.26 g (70%) of the captioned compound as crystals of a mixture of E-form and Z-form.

Example 14

Production of Ethyl (E,Z)-4-(3-Dimethylaminopropylidene)-4,10-dihydro-9-oxa-3-thiabenzo[f]azulene-6-carboxylate Hydrochloride [Compound 3]

An ethanol (50 mL) solution of the compound 4 (0.50 g) was cooled in an ice bath, thionyl chloride (1.1 mL) was then added thereto, and the mixture was stirred overnight at 80° C. The reaction mixture was allowed to air-cool, the solvents were then distilled off under a reduced pressure, and the residue was dissolved in ethyl acetate, and washed with an aqueous saturated sodium hydrogencarbonate solution and with an aqueous saturated sodium chloride solution. The washed mixture was dried over anhydrous sodium sulfate, the solvents were then distilled off under a reduced pressure, and the residue was purified by silica gel column chromatography (hexane-ethyl acetate=9:1), to give the captioned compound in a free state as an oily product of a mixture of E-form and Z-form. Subsequently, the same procedures as the method for preparing a hydrochloride in Example 11 were carried out, to give 0.37 g (64%) of the captioned compound as crystals of a mixture of E-form and Z-form.

Example 15

Production of (E)-[4-(3-Dimethylaminopropylidene)-9,10-dihydro-4H-3-thiabenzo[f]azulen-2-yl] acetic Acid Hydrochloride [Compound 5]

The same procedures as in Example 3 were carried out using (E,Z)-[3-(2-bromo-9,10-dihydro-3-thiabenzo[f]azulen-4-ylidene)propyl]-dimethylamine (2.00 g), that was obtained by the same procedures as in Example 11, from 2-bromo-9,10-dihydro-3-thiabenzo[f]azulen-4-one, to give 0.30 g (20%) of [4-(3-dimethylaminopropylidene)-9,10-dihydro-4H-3-thiabenzo[f]azulen-2-yl]acetic acid as an oily product of a mixture of E-form and Z-form. Subsequently, the same procedures as the method for preparing a hydrochloride in Example 11 were carried out, to give 0.15 g (45%) of the captioned compound as white crystals.

Example 16

Production of Ethyl (E,Z)-3-[4-(3-Dimethylaminopropylidene)-9,10-dihydro-4H-1-thiabenzo[f]azulen-2-yl]acrylate Hydrochloride [Compound 6]

To a DMF (60 mL) solution of (E,Z)-[3-(2-bromo-9,10-dihydro-1-thiabenzo[f]azulen-4-ylidene)propyl]dimethylamine (2.82 g) in a free state, that was obtained by the same procedures as in Example 11, from 2-bromo-9,10-dihydro-1-thiabenzo[f]azulen-4-one, were added ethyl acrylate (8.5 mL), triethylamine (11 mL), palladium acetate (0.14 g), and P(o-Tol)$_3$ (0.47 g) in an argon atmosphere, and the mixture was stirred overnight at 80° C. After allowing the mixture to air-cool, water was added to the reaction mixture, and the mixture was extracted with ethyl acetate. The organic layer was washed with an aqueous saturated sodium chloride solution, and thereafter dried over anhydrous sodium sulfate. The solvents were distilled off under a reduced pressure, and thereafter the residue obtained was purified by silica gel column chromatography (hexane-ethyl acetate=9:1), to give 2.29 g (77%) of the captioned compound in a free state as an oily product of a mixture of E-form and Z-form. The same procedures as the method for preparing a hydrochloride in Example 11 were carried out using this isomeric mixture (0.76 g), to give 0.57 g (68%) of the captioned compound as a mixture of E-form and Z-form.

Example 17

Production of (E,Z)-3-[4-(3-Dimethylaminopropylidene)-9,10-dihydro-4H-1-thiabenzo[f]azulen-2-yl] acrylic Acid [Compound 7]

The same procedures as in Example 9 were carried out using the compound in a free state obtained in Example 16 (1.53 g), to give 0.94 g (66%) of the captioned compound as crystals of a mixture of E-form and Z-form.

Example 18

Production of (E,Z)-4-(3-Dimethylaminopropylidene)-9,10-dihydro-4H-3-thiabenzo[f]azulene-2-carboxylic Acid [Compound 8]

The same procedures as in Examples 12 and 13 were carried out, in this order, using (E,Z)-[3-(2-bromo-9,10-dihydro-3-thiabenzo[f]azulen-4-ylidene)propyl]dimethylamine (6.33 g), that was obtained by the same procedures as in Example 11, from 2-bromo-9,10-dihydro-3-thiabenzo[f]azulen-4-one, to give 2.12 g (37%) of the captioned compound as crystals of a mixture of E-form and Z-form.

Example 19

Production of (E,Z)-4-(3-Dimethylaminopropylidene)-9,10-dihydro-4H-1-thiabenzo [f]azulene-2-carboxylic Acid-(2-hydroxyethyl)amide Hydrochloride [Compound 9]

A dichloromethane (20 mL) solution of (E,Z)-[4-(3-dimethylaminopropylidene)-9,10-dihydro-4H-1-thiabenzo[f]azulen-2-yl]carboxylic acid (0.70 g), a mixture of E-form and Z-form, that was obtained by the same procedures as in Example 18, from 2-bromo-9,10-dihydro-1-thiabenzo[f]azulen-4-one, N-hydroxysuccinimide (0.25 g) and 1-ethyl-3-(3-dimethylaminopropyl)carbodiimide (0.41 g) was stirred overnight at room temperature. The reaction mixture was washed with an aqueous saturated ammonium chloride solution, an aqueous saturated sodium hydrogencarbonate solution, and an aqueous saturated sodium chloride solution, and the solvents were distilled off under a reduced pressure. The residue was dissolved in dichloromethane (20 mL), 2-hydroxyethylamine (0.13 mL) was added thereto, and the mixture was stirred overnight at room temperature. The reaction mixture was washed with an aqueous saturated ammonium chloride solution, an aqueous saturated sodium hydrogencarbonate solution, and an aqueous saturated sodium chloride solution, and the solvents were distilled off under a reduced pressure. The resulting residue was purified by silica gel column chromatography (chloroform-methanol=19:1), to give 0.50 g (56%) of the captioned compound in a free state as an oily product of a mixture of E-form and Z-form. Subsequently, the same procedures as the method for preparing a hydrochloride in Example 11 were carried out, to give 0.29 g (34%) of the captioned compound as crystals of a mixture of E-form and Z-form.

Example 20

Production of (E,Z)-2-Bromo-4-(3-dimethylaminopropylidene)-4,9-dihydro-1-thiabenzo[f]azulen-10-one Hydrochloride [Compound 10]

The same procedures as in Example 11 were carried out using 2-bromo-10-methoxy-1-thiabenzo[f]azulen-4-one (2.04 g), to give 1.31 g (50%) of the captioned compound as crystals of a mixture of E-form and Z-form.

Example 21

Production of (E,Z)-3-[4-(3-Dimethylaminopropylidene)-9,10-dihydro-4H-3-thiabenzo[f]azulen-2-yl] acrylic Acid [Compound 11]

The same procedures as in Example 9 were carried out using the compound 1 obtained in Example 2 (0.99 g), to give 0.60 g (71%) of the captioned compound as crystals of a mixture of E-form and Z-form.

Example 22

Production of (E)-4-(3-Dimethylaminopropylidene)-9,10-dihydro-4H-3-thiabenzo[f]azulene-2-carboxylic Acid-(2-hydroxyethyl)amide [Compound 12]

The same procedures as in Example 19 were carried out using the compound 8 obtained in Example 18 (0.50 g), to give 0.14 g (25%) of the captioned compound as white crystals.

Example 23

Production of Ethyl (E,Z)-3-[4-(3-Dimethylaminopropylidene)-4,10-dihydro-9-oxa-3-thiabenzo[f]azulen-6-yl]acrylate Hydrochloride [Compound 13]

The same procedures as in Example 16 were carried out using the compound 2 obtained in Example 11 (3.05 g), to give 3.03 g (86%) of the captioned compound as crystals of a mixture of E-form and Z-form.

Example 24

Production of (E,Z)-3-[4-(3-Dimethylaminopropylidene)-4,10-dihydro-9-oxa-3-thiabenzo[f]azulen-6-yl]acrylic Acid [Compound 14]

The same procedures as in Example 9 were carried out using the compound 13 (1.92 g), to give 1.25 g (77%) of the captioned compound as crystals of a mixture of E-form and Z-form.

Example 25

Production of (E)-[4-(3-Dimethylaminopropylidene)-9,10-dihydro-4H-1-thiabenzo[f]azulen-2-yl] carboxylic Acid [Compound 15] and (Z)-[4-(3-Dimethylaminopropylidene)-9,10-dihydro-4H-1-thiabenzo[f]azulen-2-yl]carboxylic Acid [Compound 16]

The mixture of E-form and Z-form of the captioned compounds (1.20 g), that was obtained by the same procedures as in Example 11, 12, and 13, in this order, from 2-bromo-9,10-dihydro-1-thiabenzo[f]azulen-4-one, was separated and purified by the same procedures as in Example 5, to give 0.53 g (44%) and 0.28 g (23%) of the compound 15 and the compound 16, respectively, as white crystals.

Example 26

Production of (E)-[4-(3-Dimethylaminopropylidene)-9,10-dihydro-4H-1-thiabenzo[f]azulen-2-yl] acetic Acid Hydrochloride [Compound 17] and (Z)-[4-(3-Dimethylaminopropylidene)-9,10-dihydro-4H-1-thiabenzo[f]azulen-2-yl]acetic Acid Hydrochloride [Compound 18]

An oily product, a mixture of E-form or Z-form of the captioned compounds in a free state, that was obtained by the same procedures as in Examples 3 and 4, in this order, using (E,Z)-[3-(2-bromo-9,10-dihydro-1-thiabenzo[f]azulen-4-ylidene)propyl]dimethylamine (6.0 g), was formed into a solid from diethyl ether. The mixture of E-form and Z-form obtained was recrystallized from an ethyl acetate-ethanol mixed solution, to give 1.02 g (18%) of (E)-[4-(3-dimethylaminopropylidene)-9,10-dihydro-4H-1-thiabenzo[f]azulen-2-yl]acetic acid. The residue that was obtained by distilling off the solvents of the filtrate after the recrystallization was separated and purified by the same procedures as in Example 5, to give 0.25 g (4%) of (Z)-[4-(3-dimethylaminopropylidene)-9,10-dihydro-4H-1-thiabenzo[f]azulen-2-yl]acetic acid as an oily product. Subsequently, the same procedures as the method for preparing a hydrochloride in Example 11 were carried out using each of the separated and purified compounds, to give 0.80 g (73%) and 0.21 g (75%) of the compound 17 and the compound 18, respectively, as white crystals.

Example 27

Production of Ethyl (E,Z)-2-[4-(3-Dimethylamimpropylidene)-4,10-dihydro-9-oxa-3-thiabenzo[f]azulen-6-yl]-2-methylpropionate Hydrochloride [Compound 21]

Dicyclohexylamine (1.45 g) was ice-cooled under an argon atmosphere, and a 1.6 mol/L n-butyllithium-hexane solution (5.0 mL) was added dropwise thereto. Ethyl isobutyrate (0.9 mL) was added dropwise to the solution, and the mixture was stirred for 30 minutes. $Pd(dba)_2$ (0.26 g), 10% $P(t-Bu)_3$-hexane solution (1.0 mL), and (E,Z)-[3-(6-bromo-10H-9-oxo-3-thiabenzo[f]azulen-4-ylidene)propyl]dimethylamine (1.60 g) were added thereto, the mixture was heated to room temperature, and stirred overnight. An aqueous saturated ammonium chloride solution was added to the reaction mixture, and the mixture was extracted with ethyl acetate. The organic layer was washed with an aqueous saturated sodium chloride solution, and thereafter dried over anhydrous sodium sulfate. The solvents were distilled off under a reduced pressure, and the residue obtained was purified by silica gel column chromatography (hexane-ethyl acetate=19:1). Subsequently, the same procedures as the method for preparing a hydrochloride in Example 11 were carried out, to give 1.24 g (65%) of the captioned compound as crystals of a mixture of E-form and Z-form.

Example 28

Production of (E,Z)-2-[4-(3-Dimethylaminopropylidene)-4,10-dihydro-9-oxa-3-thiabenzo[f]azulen-6-yl]-2-methylpropionic acid [Compound 22]

The same procedures as in Example 9 were carried out using the compound 21 (0.98 g), to give 0.32 g (39%) of the captioned compound as crystals of a mixture of E-form and Z-form.

Example 29

Production of (E,Z)-2-[4-(3-Dimethylaminopropylidene)-9,10-dihydro-4H-1-thiabenzo[f]azulen-2-yl]-2-methylpropionic Acid [Compound 23]

The same procedures as in Example 9 were carried out using ethyl (E,Z)-2-[4-(3-dimethylaminopropylidene)-9,10-dihydro-4H-1-thiabenzo[f]azulen-2-yl]-2-methylpropionate (1.03 g), that was obtained by a reaction using a palladium catalyst by the same procedures as in Example 27, from (E,Z)-[3-(2-bromo-9,10-dihydro-1-thiabenzo[f]azulen-4- ylidene)propyl]dimethylamine, to give 0.32 g (33%) of the captioned compound as crystals of a mixture of E-form and Z-form.

Example 30

Production of Ethyl (E,Z)-2-[4-(3-Dimethylaminopropylidene)-10-oxo-9,10-dihydro-4H-1-thiabenzo[f]azulen-2-yl]-2-methylpropionate Hydrochloride [Compound 24]

The same procedures as in Example 27 were carried out using 2-bromo-4-cyclopropyl-10-methoxy-4H-1-thiabenzo[f]azulen-4-ol (3.20 g), that was obtained by the same procedures as in Example 6, from 2-bromo-10-methoxy-1-thiabenzo[f]azulen-4-one, to give 1.78 g (50%) of ethyl (2-cyclopropyl-4-hydroxy-10-methoxy-4H-1-thiabenzo[f]azulen-2-yl)-2-methylpropionate as an oily product of a mixture of E-form and Z-form. Subsequently, the same procedures as the method for preparing a hydrochloride in Example 11 were carried out, to give 0.67 g (33%) of the captioned compound as an amorphous solid of a mixture of E-form and Z-form.

Example 31

Production of (E)-{2-Methyl-2-[4-(3-methylaminopropylidene)-4,10-dihydro-9-oxa-3-thiabenzo[f]azulen-6-yl]}propionic Acid [Compound 25]

The same procedures as in Example 9 were carried out on the compound that was obtained by the same procedures as in Example 27 (2.74 g), from (E,Z)-[3-(6-bromo-10H-9-oxa-3-thiabenzo[f]azulen-4-ylidene)propyl]methylamine, to give 1.68 g (66%) of the captioned compound as a mixture of E-form and Z-form. This isomeric mixture was used and separated and purified by the same procedures as in Example 5, to give 0.60 g (34%) of the captioned compound.

Example 32

Production of (Z)-[4-(3-Dimethylaminopropylidene)-4,10-dihydro-9-oxa-1-thiabenzo[f]azulen-6-yl]acetic Acid [Compound 28] and (E)-[4-(3-Dimethylaminopropylidene)-4,10-dihydro-9-oxa-1-thiabenzo[f]azulen-6-yl]acetic Acid [Compound 29]

The mixture of E-form and Z-form of the captioned compounds (1.63 g), that was obtained by the same procedures as in Examples 11 and 9, in this order, from methyl (4-oxo-4,10-dihydro-9-1-thiabenzo[f]azulen-6-yl)acetate, was separated and purified by the same procedures as in Example 5, to give 0.39 g (23%) and 0.58 g (36%) of the compound 28 and the compound 29, respectively, as white crystals.

Example 33

Production of (E)-[4-(3-Ethylmethylaminopropylidene)-4,10-dihydro-9-oxa-3-thiabenzo[f]azulen-6-yl]acetic Acid [Compound 30] and (Z)-[4-(3-Ethylmethylaminopropylidene)-4,10-dihydro-9-oxa-3-thiabenzo[f]azulen-6-yl]acetic Acid [Compound 31]

The mixture of E-form and Z-form of the captioned compounds (1.00 g), that was obtained by the same procedures as in Examples 8 and 9, in this order, from the compound obtained in Example 7 and N-ethylmethylamine, was separated and purified by the same procedures as in Example 5, to give 0.21 g (21%) and 0.09 g (9%) of the compound 30 and the compound 31, respectively, as white crystals.

Example 34

Production of (E)-{4-[3-(Morpholin-4-yl)propylidene]-4,10-dihydro-9-oxa-3-thiabenzo[f]azulen-6-yl]acetic Acid [Compound 32] and (Z)-{4-[3-(Morpholin-4-yl)propylidene]-4,10-dihydro-9-oxa-3-thiabenzo[f]azulen-6-yl]acetic Acid [Compound 33]

The mixture of E-form and Z-form of the captioned compounds (1.52 g), that was obtained by the same procedures as in Examples 8 and 9, in this order, from the compound obtained in Example 7 and morpholine, was separated and purified by the same procedures as in Example 5, to give 0.42 g (28%) and 0.15 g (10%) of the compound 32 and the compound 33, respectively, as white crystals.

Example 35

Production of (E)-{4-[3-(Piperidin-1-yl)propylidene]-4,10-dihydro-9-oxa-3-thiabenzo[f]azulen-6-yl}acetic Acid [Compound 34] and (Z)-{4-[3-(Piperidin-1-yl)propylidene]-4,10-dihydro-9-oxa-3-thiabenzo[f]azulen-6-yl}acetic Acid [Compound 35]

The mixture of E-form and Z-form of the captioned compounds (1.25 g), that was obtained by the same procedures as in Examples 8 and 9, in this order, from the compound obtained in Example 7 and piperidine, was separated and purified by the same procedures as in Example 5, to give 0.70 g (56%) and 0.08 g (6%) of the compound 34 and the compound 35, respectively, as white crystals.

Example 36

Production of (E)-4-{4-[3-(Pyrrolidin-1-yl)propylidene]-4,10-dihydro-9-oxa-3-thiabenzo[f]azulen-6-yl}butyric Acid [Compound 36] and (Z)-4-{4-[3-(Pyrrolidin-1-yl)propylidene]-4,10-dihydro-9-oxa-3-thiabenzo[f]azulen-6-yl}butyric Acid [Compound 37]

The mixture of E-form and Z-form of the captioned compounds (1.31 g), that was obtained by the same procedures as in Examples 6, 7, 8, and 9, in this order, from methyl 4-(4-oxo-4,10-dihydro-9-oxa-3-thiabenzo[f]azulen-6-yl)butyrate, was separated and purified by the same procedures as in Example 5, to give 0.60 g (46%) and 0.16 g (12%) of the compound 36 and the compound 37, respectively, as amorphous solids.

Example 37

Production of (E)-[4-(3-Ethylaminopropylidene)-4,10-dihydro-9-oxa-3-thiabenzo[f]azulen-6-yl]acetic Acid [Compound 38] and (Z)-[4-(3-Ethylaminopropylidene)-4,10-dihydro-9-oxa-3-thiabenzo[f]azulen-6-yl]acetic Acid [Compound 39]

The mixture of E-form and Z-form of the captioned compounds (0.66 g), that was obtained by the same procedures as in Examples 8 and 9, in this order, from the compound obtained in Example 7 and ethylamine hydrochloride, was separated and purified by the same procedures as in Example 5, to give 0.46 g (70%) and 0.08 g (12%) of the compound 38 and the compound 39, respectively, as white crystals.

Example 38

Production of (E)-[4-(3-Benzylmethylaminopropylidene)-4,10-dihydro-9-oxa-3-thiabenzo[f]azulen-6-yl]acetic Acid [Compound 40] and (Z)-[4-(3-Benzylmethylaminopropylidene)-4,10-dihydro-9-oxa-3-thiabenzo[f]azulen-6-yl]acetic Acid [Compound 41]

The mixture of E-form and Z-form of the captioned compounds (1.54 g), that was obtained by the same procedures as in Examples 8 and 9, in this order, from the compound obtained in Example 7 and N-benzylmethylamine, was separated and purified by the same procedures as in Example 5, to give 0.65 g (42%) and 0.10 g (6%) of the compound 40 and the compound 41, respectively, as white crystals.

Example 39

Production of (E)-[4-(3-Benzylaminopropylidene)-4,10-dihydro-9-oxa-3-thiabenzo[f]azulen-6-yl]acetic Acid [Compound 42] and (Z)-[4-(3-Benzylaminopropylidene)-4,10-dihydro-9-oxa-3-thiabenzo[f]azulen-6-yl]acetic Acid [Compound 43]

The mixture of E-form and Z-form of the captioned compounds (1.51 g), that was obtained by the same procedures as in Examples 8 and 9, in this order, from the compound obtained in Example 7 and benzylamine, was separated and purified by the same procedures as in Example 5, to give 0.62 g (41%) of the compound 42 as an amorphous solid and 0.23 g (15%) of the compound 43 as white crystals.

Example 40

Production of (E)-[4-(3-Cyclopentylaminopropylidene)-4,10-dihydro-9-oxa-3-thiabenzo[f]azulen-6-yl]acetic Acid [Compound 44] and (Z)-[4-(3-Cyclopentylaminopropylidene)-4,10-dihydro-9-oxa-3-thiabenzo[f]azulen-6-yl]acetic Acid [Compound 45]

The mixture of E-form and Z-form of the captioned compounds (1.00 g), that was obtained by the same procedures as in Examples 8 and 9, in this order, from the compound obtained in Example 7 and cyclopentylamine, was separated and purified by the same procedures as in Example 5, to give 0.54 g (54%) and 0.10 g (10%) of the compound 44 and the compound 45, respectively, as white crystals.

Example 41

Production of (E)-[4-(3-Isopropylaminopropylidene)-4,10-dihydro-9-oxa-3-thiabenzo[f]azulen-6-yl]acetic Acid [Compound 46] and (Z)-[4-(3-Isopropylaminopropylidene)-4,10-dihydro-9-oxa-3-thiabenzo[f]azulen-6-yl]acetic Acid [Compound 47]

The mixture of E-form and Z-form of the captioned compounds (2.02 g), that was obtained by the same procedures as in Examples 8 and 9, in this order, from the compound obtained in Example 7 and isopropylamine, was separated and purified by the same procedures as in Example 5, to give 0.38 g (19%) and 0.05 g (2%) of the compound 46 and the compound 47, respectively, as white crystals.

Example 42

Production of (E)-3-[4-(3-Dimethylaminopropylidene)-4,10-dihydro-9-oxa-3-thiabenzo[f]azulen-6-yl]propionic Acid [Compound 48] and (Z)-3-[4-(3-Dimethylaminopropylidene)-4,10-dihydro-9-oxa-3-thiabenzo[f]azulen-6-yl]propionic Acid [Compound 49]

The same procedures as in Examples 6 and 7 were carried out, from methyl 3-(4-oxo-4,10-dihydro-9-oxa-3-thiabenzo[f]azulen-6-yl)propionate, to give methyl (E,Z)-3-[4-(3-bromopropylidene)-4,10-dihydro-9-oxa-3-thiabenzo[f]azulen-6-yl)propionate. The same procedures as in Examples 8 and 9 were carried out, in this order, using this mixture of E-form and Z-form and dimethylamine hydrochloride, to give a mixture of E-form and Z-form of the captioned compounds (1.32 g), and the mixture obtained was separated and purified by the same procedures as in Example 5, to give 0.33 g (25%) of the compound 48 as an amorphous solid and 0.06 g (5%) of the compound 49 as white crystals.

Example 43

Production of (E)-{4-[3-(4-Methylpiperadin-1-yl)propylidene]-4,10-dihydro-9-oxa-3-thiabenzo[f]azulen-6-yl}acetic Acid [Compound 50] and (Z)-{4-[3-(4-Methylpiperadin-1-yl)propylidene]-4,10-dihydro-9-oxa-3-thiabenzo[f]azulen-6-yl}acetic Acid [Compound 51]

The mixture of E-form and Z-form of the captioned compounds (0.61 g), that was obtained by the same procedures as in Examples 8 and 9, in this order, from the compound obtained in Example 7 and 1-methylpiperadine, was separated and purified by the same procedures as in Example 5, to give 0.25 g (41%) and 0.03 g (5%) of the compound 50 and the compound 51, respectively, as white crystals.

Example 44

Production of (E)-3-{4-[3-(Pyrrolidin-1-yl)propylidene]-4,10-dihydro-9-oxa-3-thiabenzo[f]azulen-6-yl}propionic Acid [Compound 52] and (Z)-3-{4-[3-(Pyrrolidin-1-yl)propylidene]-4,10-dihydro-9-oxa-3-thiabenzo[f]azulen-6-yl}propionic Acid [Compound 53]

The mixture of E-form and Z-form of the captioned compounds (1.21 g), that was obtained by the same procedures as in Examples 6, 7, 8, and 9, in this order, from methyl 3-(4-oxo-4,10-dihydro-9-oxa-3-thiabenzo[f]azulen-6-yl)propionate, was separated and purified by the same procedures as in Example 5, to give 0.33 g (27%) of the compound 52 as white crystals and 0.06 g (5%) of the compound 53 as an amorphous solid.

Example 45

Production of (E)-{4-[3-(4-Phenylpiperadin-1-yl)propylidene]-4,10-dihydro-9-oxa-3-thiabenzo[f]azulen-6-yl}acetic Acid [Compound 54] and (Z)-{4-[3-(4-Phenylpiperadin-1-yl)propylidene]-4,10-dihydro-9-oxa-3-thiabenzo[f]azulen-6-yl}acetic Acid [Compound 55]

The mixture of E-form and Z-form of the captioned compounds (1.08 g), that was obtained by the same procedures as in Examples 8 and 9, in this order, from the compound obtained in Example 7 and 1-phenylpiperadine, was separated and purified by the same procedures as in Example 5, to give 0.11 g (10%) and 0.05 g (5%) of the compound 54 and the compound 55, respectively, as white crystals.

Example 46

Production of (E)-3-[4-(3-Dimethylaminopropylidene)-4,10-dihydro-9-oxa-1-thiabenzo[f]azulen-6-yl]propionic Acid Hydrochloride [Compound 56] and (Z)-3-[4-(3-Dimethylaminopropylidene)-4,10-dihydro-9-oxa-1-thiabenzo[f]azulen-6-yl]propionic Acid Hydrochloride [Compound 57]

The same procedures as in Examples 6 and 7 were carried out, from methyl 3-(4-oxo-4,10-dihydro-9-oxa-1-thiabenzo[f]azulen-6-yl)propionate, to give methyl (E,Z)-3-[4-(3-bromopropylidene)-4,10-dihydro-9-oxa-1-thiabenzo[f]azulen-6-yl)propionate. The mixture of E-form and Z-form of the captioned compounds (0.89 g), that was obtained by the same procedures as in Examples 8 and 9, in this order, from this mixture E-form and Z-form and dimethylamine hydrochloride, was separated and purified by the same procedures as in Example 5, to give the compound 56 and the compound 57, which are amorphous solids, in a free state. Next, the same procedures as in the method for preparing a hydrochloride of Example 11 were carried out, to give 0.10 g (11%) and 0.08 g (9%) of the compound 56 and the compound 57, respectively, as white crystals.

Example 47

Production of (E)-3-{4-[3-(Pyrrolidin-1-yl)propylidene]-4,10-dihydro-9-oxa-1-thiabenzo[f]azulen-6-yl}propionic Acid [Compound 58] and (Z)-3-{4-[3-(Pyrrolidin-1-yl)propylidene]-4,10-dihydro-9-oxa-1-thiabenzo[f]azulen-6-yl}propionic Acid [Compound 59]

The mixture of E-form and Z-form of the captioned compounds (1.20 g), that was obtained by the same procedures as in Examples 6, 7, 8, and 9, in this order, from methyl 3-(4-oxo-4,10-dihydro-9-oxa-1-thiabenzo[f]azulen-6-yl)propionate, was separated and purified by the same procedures as in Example 5, to give 0.37 g (31%) and 0.22 g (18%) of the compound 58 and the compound 59, respectively as amorphous solids.

Example 48

Production of (E)-4-[4-(3-Dimethylaminopropylidene)-4,10-dihydro-9-oxa-3-thiabenzo[f]azulen-6-yl]butyric Acid [Compound 60] and (Z)-4-[4-(3-Dimethylaminopropylidene)-4,10-dihydro-9-oxa-3-thiabenzo[f]azulen-6-yl]butyric Acid [Compound 61]

The same procedures as in Examples 6 and 7 were carried out, from methyl 4-(4-oxo-4,10-dihydro-9-oxa-3-thiabenzo[f]azulen-6-yl)butyrate, to give methyl (E,Z)-4-[4-(3-bromopropylidene)-4,10-dihydro-9-oxa-3-thiabenzo[f]azulen-6-yl)butyrate. The same procedures as in Examples 8 and 9 were carried out, in this order, using this mixture of E-form and Z-form and dimethylamine hydrochloride, to give a mixture of E-form and Z-form of the captioned compounds (1.52 g), and the mixture obtained was separated and purified by the same procedures as in Example 5, to give 0.33 g (22%) of the compound 60 as white crystals and 0.09 g (6%) of the compound 61 as an amorphous solid.

Example 49

Production of (E)-{4-[3-(4-Oxopiperidin-1-yl)propylidene]-4,10-dihydro-9-oxa-3-thiabenzo[f]azulen-6-yl}acetic Acid [Compound 62] and (Z)-{4-[3-(4-Oxopiperidin-1-yl)propylidene]-4,10-dihydro-9-oxa-3-thiabenzo[f]azulen-6-yl}acetic Acid [Compound 63]

The mixture of E-form and Z-form of the captioned compounds (0.60 g), that was obtained by the same procedures as in Examples 8 and 9, in this order, from the compound obtained in Example 7 and 4-piperidone, was separated and purified by the same procedures as in Example 5, to give 0.28 g (47%) and 0.10 g (17%) of the compound 62 and the compound 63, respectively, as white crystals.

Example 50

Production of (E)-[4-(3-Dimethylaminopropylidene)-9,10-dihydro-4H-3-thiabenzo[f]azulen-6-yl]acetic Acid [Compound 64] and (Z)-[4-(3-Dimethylaminopropylidene)-9,10-dihydro-4H-3-thiabenzo[f]azulen-6-yl]acetic Acid Hydrochloride [Compound 65]

The same procedures as in Examples 6 and 7 were carried out, from ethyl (4-oxo-9,10-dihydro-4H-3-thiabenzo[f]azulen-6-yl)acetate, to give ethyl (E,Z)-[4-(3-bromopropylidene)-9,10-dihydro-4H-3-thiabenzo[f]azulen-6-yl]acetate. A mixture of E-form and Z-form of the captioned compounds (0.91 g), that was obtained by the same procedures as in Examples 8 and 9, in this order, using this mixture of E-form and Z-form and a 50% aqueous dimethylamine solution, was separated and purified by the same procedures as in Example 5, to give 0.35 g (38%) of the compound 64 as white crystals, and 0.20 g (22%) of the compound 65 in a free state as an amorphous solid. The same procedures as in a method for preparing a hydrochloride of Example 11 from the compound 65 in a free state, to give 0.15 g (68%) of the captioned compound 65 as white crystals.

Example 51

Production of (E)-{4-[3-([1,4']Bipiperidin-1'-yl)propylidene]-4,10-dihydro-9-oxa-3-thiabenzo[f]azulen-6-yl}acetic Acid Diformate [Compound 66] and (Z)-{4-[3-([1,4']Bipiperidin-1'-yl)propylidene]-4,10-dihydro-9-oxa-3-thiabenzo[f]azulen-6-yl}acetic Acid Diformate [Compound 67]

The mixture of E-form and Z-form of the captioned compounds (0.83 g), that was obtained by the same procedures as in Examples 8 and 9, in this order, using the compound obtained in Example 7 and 4-piperidinopiperidine, was separated and purified by the same procedures as in Example 5, to give 0.44 g (53%) and 0.14 g (16%) of the compound 66 and the compound 67, respectively, as amorphous solids.

Example 52

Production of (E,Z)-{4-[3-(Thiomorpholin-4-yl)propylidene]-4,10-dihydro-9-oxa-3-thiabenzo[f]azulen-6-yl}acetic Acid [Compound 68]

The same procedures as in Examples 8 and 9, in this order, were carried out, from the compound obtained in Example 7 (2.00 g) and thiomorpholine, to give 0.83 g (37%) of the captioned compound as crystals of a mixture of E-form and Z-form.

Example 53

Production of (E,Z)-2-Methyl-2-{4-[3-(pyrrolidin-1-yl)propylidene]-9,10-dihydro-4H-1-thiabenzo[f]azulen-2-yl}propionic Acid [Compound 69]

The same procedures as in Examples 27 and 9, in this order, were carried out using (E,Z)-1-[3-(6-bromo-9,10-dihydro-3-thiabenzo[f]azulen-4-ylidene)propyl]pyrrolidine (3.01 g), that was obtained by the same procedures as in Examples 6, 7, and 8, in this order, from 6-bromo-9,10-dihydro-3-thiabenzo[f]azulen-4-one, to give 1.53 g (51%) of the captioned compound as crystals of a mixture of E-form and Z-form.

Example 54

Production of (E)-{4-[3-(Pyrrolidin-1-yl)propylidene]-4,10-dihydro-9-oxa-3-thiabenzo[f]azulen-6-yl}acetic Acid Hydrochloride [Compound 70]

The same procedures as in the method for preparing a hydrochloride of Example 11 were carried out, using the compound 26 (1.09 g) obtained in Example 10, to give 1.10 g (92%) of the captioned compound as white crystals.

Example 55

Production of (Z)-{4-[3-(Pyrrolidin-1-yl)propylidene]-4,10-dihydro-9-oxa-3-thiabenzo[f]azulen-6-yl}acetic Acid Hydrochloride [Compound 71]

The same procedures as in the method for preparing a hydrochloride of Example 11 were carried out, using the compound 27 (0.31 g) obtained in Example 10, to give 0.31 g (90%) of the captioned compound as white crystals.

The data of the properties for the compounds of the present invention produced in the above Examples are shown in Tables 1 through 8.

TABLE 1

| Compound No. | Properties |
|---|---|
| Compound 1 | Mp. 108° C. (dec.). $^1$H-NMR (DMSO-$d_6$) δ: 1.16-1.25 (m, 3H), 1.99-2.66 (m, 10H), 2.94-3.02 (m, 4H), 4.02-4.18 (m, 2H), 5.73-6.12 (m, 1H), 6.38-6.45 (m, 1H), 7.12-7.48 (m, 6H). |
| Compound 2 | $^1$H-NMR (DMSO-$d_6$) δ: 2.63-2.95 (m, 8H), 3.20-3.27 (m, 2H), 5.10-5.17 (m, 2H), 5.92-6.05 (m, 1H), 6.81-7.61 (m, 5H), 10.18-10.49 (m, 1H). |
| Compound 3 | $^1$H-NMR (DMSO-$d_6$) δ: 1.30-1.34 (m, 3H), 2.64-2.91 (m, 8H), 3.20-3.28 (m, 2H), 4.28-4.34 (m, 2H), 5.17-5.24 (m, 2H), 6.03-6.08 (m, 1H), 6.83-7.99 (m, 5H), 10.16-10.35 (m, 1H). |
| Compound 4 | $^1$H-NMR (DMSO-$d_6$) δ: 2.13-2.19 (m, 6H), 2.35-2.63 (m, 4H), 5.13-5.21 (m, 2H), 6.04-6.12 (m, 1H), 6.80-7.91 (m, 5H). |
| Compound 5 | Mp. 220° C. (dec.). MS (EI): m/z 342 [M$^+$ + 1]. $^1$H-NMR (DMSO-$d_6$) δ: 2.50-3.45 (m, 14H), 5.50-5.92 (m, 1H), 6.83-6.86 (m, 1H), 7.15-7.33 (m, 4H), 10.17 (br, 1H), 12.53 (brs, 1H). |
| Compound 6 | $^1$H-NMR (DMSO-$d_6$) δ: 1.22-1.25 (m, 3H), 2.50-3.25 (m, 14H), 4.14-4.18 (m, 2H), 5.59-6.14 (m, 2H), 7.18-7.51 (m, 5H), 7.68-7.79 (m, 1H), 10.10 (brs, 1H). |
| Compound 7 | $^1$H-NMR (DMSO-$d_6$) δ: 2.02-3.22 (m, 14H), 5.65-6.04 (m, 2H), 7.14-7.68 (m, 6H). |
| Compound 8 | $^1$H-NMR (DMSO-$d_6$) δ: 2.09-2.20 (m, 6H), 2.30-3.12 (m, 8H), 5.72-6.06 (m, 1H), 7.12-7.33 (m, 4H), 7.98-8.14 (m, 1H). |

TABLE 1-continued

| Compound No. | Properties |
|---|---|
| Compound 9 | MS (EI): m/z 371 [M$^+$ + 1], $^1$H-NMR (DMSO-$d_6$) δ: 2.30-3.51 (m, 18H), 4.69-4.83 (br, 1H), 5.57-6.00 (m, 1H), 7.14-7.34 (m, 4H), 7.79-7.83 (m, 1H), 8.39-8.72 (m, 1H), 9.99-10.05 (m, 1H). |
| Compound 10 | $^1$H-NMR (DMSO-$d_6$) δ: 2.52-3.25 (m, 10H), 3.69-4.28 (m, 2H), 5.97-6.44 (m, 1H), 7.29-7.44 (m, 4H), 7.57-7.59 (m, 1H), 10.34 (brs, 1H). |
| Compound 11 | $^1$H-NMR (DMSO-$d_6$) δ: 2.08-2.19 (m, 6H), 2.22-3.40 (m, 8H), 6.02-6.35 (m, 2H), 7.14-7.42 (m, 5H), 7.85-8.05 (m, 1H). |
| Compound 12 | MS (EI): m/z 371 [M$^+$ + 1]. $^1$H-NMR (DMSO-$d_6$) δ: 2.03 (s, 6H), 2.13-2.35 (m, 4H), 2.50-3.22 (m, 6H), 3.42-3.46 (m, 2H), 4.65 (t, J = 5.6 Hz, 1H), 6.01-6.04 (m, 1H), 7.15-7.32 (m, 4H), 7.62 (s, 1H), 8.03-8.06 (m, 1H). |

TABLE 2

| Compound No. | Properties |
|---|---|
| Compound 13 | $^1$H-NMR (DMSO-$d_6$) δ: 1.24-1.27 (m, 3H), 2.66-3.39 (m, 10H), 4.16-4.21 (m, 2H), 5.13-5.20 (m, 2H), 6.02-6.05 (m, 1H), 6.60-7.81 (m, 7H), 10.12-10.53 (m, 1H). |
| Compound 14 | $^1$H-NMR (DMSO-$d_6$) δ: 2.20-2.25 (m, 6H), 2.41-2.68 (m, 4H), 5.11-5.17 (m, 2H), 6.01-6.09 (m, 1H), 6.46-6.53 (m, 1H), 6.80-7.72 (m, 6H). |
| Compound 15 | Mp. 154°-156° C. $^1$H-NMR (DMSO-$d_6$) δ: 2.32-2.35 (m, 8H), 2.83-3.20 (m, 6H), 6.05 (t, J = 7.3 Hz, 1H), 7.15-7.36 (m, 5H). |
| Compound 16 | Mp. 160°-163° C. MS (EI): m/z 328 [M$^+$ + 1]. $^1$H-NMR (DMSO-$d_6$) δ: 2.46-3.09 (m, 14H), 5.52-5.55 (m, 1H), 7.14-7.29 (m, 5H). |
| Compound 17 | Mp. 218° C.(dec.). MS (EI): m/z 342 [M$^+$ + 1]. $^1$H-NMR (DMSO-$d_6$) δ: 2.36-3.70 (m, 16H), 5.88-5.92 (m, 1H), 6.84 (s, 1H), 7.15-7.34 (m, 4H), 10.18 (br, 1H), 12.55 (brs, 1H). |
| Compound 18 | Mp. 242° C.(dec.). MS (EI): m/z 342 [M$^+$ + 1]. $^1$H-NMR (DMSO-$d_6$) δ: 2.71-2.74 (m, 8H), 3.00-3.22 (m, 6H), 3.76 (s, 2H), 5.53 (t, J = 7.2 Hz, 1H), 6.84 (s, 1H), 7.14-7.29 (m, 4H), 10.31 (brs, 1H), 12.56 (brs, 1H). |
| Compound 19 | Mp. 182°-184° C. MS (EI): m/z 344 [M$^+$ + 1]. $^1$H-NMR (DMSO-$d_6$) δ: 2.12 (s, 6H), 2.35-2.39 (m, 4H), 3.55 (s, 2H), 5.05 (s, 2H), 6.03-6.06 (m, 1H), 6.77-6.78 (m, 1H), 7.09-7.11 (m, 1H), 7.19-7.32 (m, 3H). |
| Compound 20 | Mp. 188°-190° C. MS (EI): m/z 344 [M$^+$ + 1]. $^1$H-NMR 2(DMSO-$d_6$) δ: .19 (s, 6H), 2.46-2.68 (m, 4H), 3.53 (s, 2H), 5.12 (s, 2H), 5.85 (t, J = 7.3 Hz, 1H), 6.89-6.98 (m, 2H), 7.13-7.15 (m, 2H), 7.52-7.53 (m, 1H). |
| Compound 21 | MS (EI): m/z 400 [M$^+$ + 1]. $^1$H-NMR (DMSO-$d_6$) δ: 1.11-1.15 (m, 3H), 1.49-1.52 (m, 6H), 2.63-3.27 (m, 10H), 4.05-4.10 (m, 2H), 5.08-5.15 (m, 2H), 5.80-6.03 (m, 1H), 6.80-7.61 (m, 5H), 10.33-10.52 (m, 1H). |
| Compound 22 | MS (EI): m/z 372 [M$^+$ + 1]. $^1$H-NMR (DMSO-$d_6$) δ: 1.44-1.46 (m, 6H), 2.22-2.67 (m, 10H), 5.06-5.12 (m, 2H), 5.82-6.06 (m, 1H), 6.78-7.53 (m, 5H). |
| Compound 23 | MS (EI): m/z 370 [M$^+$ + 1]. $^1$H-NMR (DMSO-$d_6$) δ: 1.48-1.52 (m, 6H), 2.05-3.08 (m, 14H), 5.56-5.96 (m, 1H), 6.98-6.77 (m, 1H), 7.11-7.29 (m, 4H). |

TABLE 3

| Compound No. | Properties |
|---|---|
| Compound 24 | MS (EI): m/z 412 [M$^+$ + 1]. $^1$H-NMR (DMSO-$d_6$) δ: 1.14-1.19 (m, 3H), 1.59-1.62 (m, 6H), 2.50-3.39 (m, 10H), 3.66-3.72 (m, 1H), 4.07-4.11 (m, 2H), 4.23-4.26 (m, 1H), 5.93-6.34 (m, 1H), 7.20-7.43 (m, 5H), 9.87-9.93 (m, 1H). |
| Compound 25 | Mp. 218° C.(dec). MS (EI): m/z 357 [M$^+$]. $^1$H-NMR (DMSO-$d_6$) δ: 1.38 (s, 6H), 2.36-2.42 (m, 2H), 2.91-2.95 (m, 2H). 5.06 (s, 2H), 6.01 (t, J = 8.0 Hz, 1H), 6.81-6.82 (m, 1H), 7.06-7.37 (m, 4H). |
| Compound 26 | Mp. 225°-227° C. MS (EI): m/z 370 [M$^+$ + 1]. $^1$H-NMR (DMSO-$d_6$) δ: 1.15-1.19 (m, 4H), 2.39-2.59 (m, 8H), 3.54 (s, 2H), 5.05 (s, 2H), 6.03-6.07 (m, 1H), 6.77-6.69 (m, 1H), 7.09-7.32 (m, 4H). |

TABLE 3-continued

| Compound No. | Properties |
|---|---|
| Compound 27 | Mp. 203°-205° C. MS (EI): m/z 370 [M$^+$ + 1]. $^1$H-NMR (DMSO-d$_6$) δ: 1.6-1.69 (m, 4H), 2.49-2.71 (m, 8H), 3.60 (s, 2H), 5.12 (s, 2H), 5.84-5.88 (m, 1H), 6.89-7.16 (m, 4H), 7.52-7.54 (m, 1H). |
| Compound 28 | Mp. 168° C.-70° C. $^1$H-NMR (DMSO-d$_6$) δ: 2.12 (s, 6H), 2.34-2.39 (m, 4H), 3.54 (s, 2H), 5.17 (s, 2H), 6.07 (t, J = 7.1 Hz, 1H), 7.07-7.19 (m, 4H), 7.39-7.41 (m, 1H). |
| Compound 29 | Mp. 176°-179° C. $^1$H-NMR (DMSO-d$_6$) δ: 2.17 (s, 6H), 2.40-2.46 (m, 4H), 3.50 (s, 2H), 5.24 (s, 2H), 5.88-5.91 (m, 1H), 6.84-6.86 (m, 1H), 7.08-7.17 (m, 3H), 7.49-7.50 (m, 1H). |
| Compound 30 | Mp. 179°-180° C. $^1$H-NMR (DMSO-d$_6$) δ: 0.96 (t, J = 7.2 Hz, 3H), 2.12 (s, 3H), 2.35-2.39 (m, 4H), 2.45-2.50 (m, 2H), 3.55 (s, 2H), 5.05 (s, 2H), 6.04-6.07 (m, 1H), 6.77-6.78 (m, 1H), 7.09-7.32 (m, 4H). |
| Compound 31 | Mp. 181°-182° C. $^1$H-NMR (DMSO-d$_6$) δ: 0.98 (t, J = 7.2 Hz, 3H), 2.17 (s, 3H), 2.39 (q, J = 7.1 Hz, 2H), 2.50-2.67 (m, 4H), 3.52 (s, 2H), 5.12 (s, 2H), 5.85 (t, J = 7.2 Hz, 1H), 6.89-7.15 (m, 4H), 7.52-7.53 (m, 1H). |
| Compound 32 | Mp. 172°-174° C. $^1$H-NMR (DMSO-d$_6$) δ: 2.30-2.40 (m, 8H), 3.52-3.58 (m, 6H), 5.05 (s, 2H), 6.05-6.07 (m, 1H), 6.77-6.78 (m, 1H), 7.10-7.32 (m, 4H). |
| Compound 33 | Mp. 193°-194° C. $^1$H-NMR (DMSO-d$_6$) δ: 2.37-2.70 (m, 8H), 3.53-3.57 (m, 6H), 5.12 (s, 2H), 5.86 (t, J = 7.4 Hz, 1H), 6.89-7.16 (m, 4H), 7.52-7.53 (m, 1H). |

TABLE 4

| Compound No. | Properties |
|---|---|
| Compound 34 | Mp. 138°-140° C. $^1$H-NMR (DMSO-d$_6$) δ: 1.35-1.50 (m, 6H), 2.38-2.50 (m, 8H), 3.55 (s, 2H), 5.05 (s, 2H), 6.01-6.05 (m, 1H), 6.77-6.79 (m, 1H), 7.09-7.32 (m, 4H). |
| Compound 35 | Mp. 180°-181° C. $^1$H-NMR (DMSO-d$_6$) δ: 1.36-1.49 (m, 6H), 2.37-2.69 (m, 8H), 3.52 (s, 2H), 5.12 (s, 2H), 5.84 (t, J = 7.4 Hz, 1H), 6.89-7.15 (m, 4H), 7.52-7.53 (m, 1H). |
| Compound 36 | $^1$H-NMR (DMSO-d$_6$) δ: 1.70-1.80 (m, 6H), 2.13-2.16 (m, 2H), 2.41-2.71 (m, 10H), 5.04 (s, 2H), 6.03 (t, J = 7.5 Hz, 1H), 6.77-6.78 (m, 1H), 7.08-7.32 (m, 4H). |
| Compound 37 | $^1$H-NMR (DMSO-d$_6$) δ: 1.65-1.78 (m, 6H), 2.20-2.22 (m, 2H), 2.49-2.71(m, 10H), 5.11 (s, 2H), 5.85-5.88 (m, 1H), 6.88-7.09 (m, 4H), 7.52-7.53 (m, 1H). |
| Compound 38 | Mp. 200°-202° C. $^1$H-NMR (DMSO-d$_6$) δ: 1.12 (t, J = 7.2 Hz, 3H), 2.43-2.50 (m, 2H), 2.80 (q, J = 7.2 Hz, 2H), 2.90-2.94 (m, 2H), 3.41 (s, 4H), 5.05 (s, 2H), 6.03 (t, J = 7.7 Hz, 1H), 6.79-6.81 (m, 1H), 7.04-7.35 (m, 4H). |
| Compound 39 | Mp. 256°-258° C. $^1$H-NMR (DMSO-d$_6$) δ: 1.03 (t, J = 7.2 Hz, 3H), 2.50-2.79 (m, 6H), 3.50 (s, 2H), 5.12 (s, 2H), 5.85-5.88 (m, 1H), 6.88-7.18 (m, 4H), 7.52-7.54 (m, 1H). |
| Compound 40 | Mp. 92°-94° C. $^1$H-NMR (DMSO-d$_6$) δ: 2.10 (s, 3H), 2.36-2.50 (m, 4H), 3.47 (s, 2H), 3.57 (s, 2H), 5.06 (s, 2H), 6.07 (t, J = 7.1 Hz, 1H), 6.77-6.79 (m, 1H), 7.10-7.33 (m, 9H). |
| Compound 41 | Mp. 98°-99° C. $^1$H-NMR (DMSO-d$_6$) δ: 2.19 (s, 3H), 2.63-2.72 (m, 4H), 3.52-3.54 (m, 4H), 5.11 (s, 2H), 5.86 (t, J =7.2 Hz, 1H), 6.88-6.99 (m, 2H), 7.14-7.31 (m, 7H), 7.51-7.52 (m, 1H). |

TABLE 5

| Compound No. | Properties |
|---|---|
| Compound 42 | $^1$H-NMR (DMSO-d$_6$) δ: 2.38-2.45 (m, 2H), 2.69 (t, J = 7.0 Hz, 2H), 3.52 (s, 2H), 3.74 (s, 2H), 5.05 (s, 2H), 6.08 (t, J = 7.4 Hz, 1H), 6.79 (d, J = 5.1 Hz, 1H), 7.10 (d, J = 7.9 Hz, 1H), 7.18-7.7.26 (m, 2H), 7.27-7.26 (m, 5H). |
| Compound 43 | Mp. 221° C.(dec.). $^1$H-NMR (DMSO-d$_6$) δ: 2.62-2.76 (m, 4H), 3.50 (s, 2H), 3.73 (s, 2H), 5.10 (s, 2H), 5.88 (t, J = 6.6 Hz, 1H), 6.88 (d, J = 5.0 Hz, 1H), 6.96 (d, J = 8.0 Hz, 1H), 7.14 (d, J = 8.0 Hz, 1H), 7.17 (s, 1H), 7.18-7.36 (m, 5H), 7.51 (d, J = 5.0 Hz, 1H). |

TABLE 5-continued

| Compound No. | Properties |
|---|---|
| Compound 44 | $^1$H-NMR (DMSO-d$_6$) δ: 1.48-1.53 (m, 4H), 1.63-1.68 (m, 1H), 1.85-1.87 (m, 1H), 2.49-2.52 (m, 2H), 2.93-2.96 (m, 2H), 3.29-3.31 (m, 1H), 3.47 (s, 2H), 5.06 (s, 2H), 6.04 (t, J = 7.3 Hz, 1H), 6.79 (d, J = 5.2 Hz, 1H), 7.08 (d, J = 8.0 Hz, 1H), 7.18-7.22 (m, 2H), 7.34 (d, J = 5.2 Hz, 1H). |
| Compound 45 | $^1$H-NMR (DMSO-d$_6$) δ: 1.31-1.33 (m, 2H), 1.44-1.45 (m, 2H), 1.58-1.60 (m, 2H), 1.71-1.74 (m, 2H), 2.64-2.73 (m, 4H), 3.04-3.07 (m, 1H), 3.48 (s, 2H), 5.12 (s, 2H), 5.86 (t, J = 7.1 Hz, 1H), 6.88 (d, J = 5.2 Hz, 1H), 6.96 (d, J = 8.1 Hz, 1H), 7.12-7.17 (m, 2H), 7.52 (d, J = 5.2 Hz, 1H). |
| Compound 46 | $^1$H-NMR (DMSO-d$_6$) δ: 1.14 (d, J = 6.2 Hz, 1H), 2.38-2.45 (m, 2H), 2.89 (t, J = 8.0 Hz, 2H), 3.01-3.08 (m, 1H), 3.36 (s, 2H), 5.05 (s, 2H), 6.04 (d, J = 7.7 Hz, 1H), 6.80 (d, J = 5.1 Hz, 1H), 7.02-7.14 (m, 2H), 7.24 (s, 1H), 7.35 (d, J = 5.1 Hz, 1H). |
| Compound 47 | $^1$H-NMR (DMSO-d$_6$) δ: 1.05 (d, J = 6.2 Hz, 6H), 2.63-2.98 (m, 5H), 3.49 (s, 2H), 5.12 (s, 2H), 5.85 (t, J = 7.2 Hz, 1H), 6.90 (d, J = 5.2 Hz, 1H), 6.97 (d, J = 8.2 Hz, 1H), 7.12-7.19 (m, 2H), 7.55 (d, J = 5.0 Hz, 1H). |
| Compound 48 | $^1$H-NMR (DMSO-d$_6$) δ: 2.35-2.44 (m, 10H), 2.72-2.75 (m, 2H), 2.80-2.81 (m, 2H), 5.03 (s, 2H), 5.96 (t, J = 7.8 Hz, 1H), 6.77 (d, J= 5.3 Hz, 1H), 7.07 (d, J = 7.8 Hz, 1H), 7.15-7.17 (m, 2H), 7.31 (d, J = 5.3 Hz, 1H), 8.17 (s, 1H). |
| Compound 49 | $^1$H-NMR (DMSO-d$_6$) δ: 2.20 (s, 6H), 2.47-4.52 (m, 4H), 2.64-2.69 (m, 2H), 2.76-2.79 (m, 2H), 5.10 (s, 2H), 5.84 (t, J = 7.1 Hz, 1H), 6.87 (d, J = 5.1 Hz, 1H), 6.94 (d, J = 8.5 Hz, 1H), 7.11-7.14 (m, 2H), 7.51 (d, J = 5.1 Hz, 1H). |

TABLE 6

| Compound No. | Properties |
|---|---|
| Compound 50 | $^1$H-NMR (DMSO-d$_6$) δ: 1.99 (s, 3H), 2.17-2.41 (m, 12H), 3.57 (s, 2H), 5.05 (s, 2H), 6.04 (t, J = 7.5 Hz, 1H), 6.77 (d, J = 4.9 Hz, 1H), 7.10-7.12 (m, 1H), 7.20-7.22 (m, 2H), 7.31-7.32 (m, 1H). |
| Compound 51 | $^1$H-NMR (DMSO-d$_6$) δ: 2.15 (s, 3H), 2.30-2.49 (m, 10H), 2.65-2.66 (m, 2H), 3.53 (s, 2H), 5.12 (s, 2H), 5.82-5.85 (m, 1H), 6.89 (d, J = 4.6 Hz, 1H), 6.97 (d, J = 7.6 Hz, 1H), 7.10-7.15 (m, 2H), 7.52 (d, J = 4.6 Hz, 1H). |
| Compound 52 | $^1$H-NMR (DMSO-d$_6$) δ: 1.70-1.83 (m, 4H), 2.22-2.30 (m, 2H), 2.41-2.50 (m, 2H), 2.75-2.80 (m, 2H), 2.84-3.00 (m, 6H), 5.02 (s, 2H), 5.94 (t, J = 8.0 Hz, 1H), 6.78 (d, J = 5.0 Hz, 1H), 7.07 (d, J = 8.0 Hz, 1H), 7.15 (d, J = 8.0 Hz, 1H), 7.18 (s, 1H), 7.33 (d, J = 5.0 Hz, 1H). |
| Compound 53 | $^1$H-NMR (DMSO-d$_6$) δ: 1.62-1.75 (m, 4H), 2.50-2.80 (m, 12H), 5.10 (s, 2H), 5.86 (t, J = 6.6 Hz, 1H), 6.88 (d, J = 5.0 Hz, 1H), 6.91 (d, J = 8.0 Hz, 1H), 7.10-7.15 (m, 2H), 7.52 (d, J = 5.0 Hz, 1H). |
| Compound 54 | $^1$H-NMR (DMSO-d$_6$) δ: 2.39-2.55 (m, 8H), 3.06-3.12 (m, 4H), 3.59 (s, 2H), 5.06 (s, 2H), 6.08 (t, J = 7.2 Hz, 1H), 6.73-6.79 (m, 2H), 6.90 (d, J = 8.1 Hz, 2H), 7.12 (d, J = 8.5 Hz, 1H), 7.16-7.24 (m, 4H), 7.32 (d, J = 5.2 Hz, 1H). |
| Compound 55 | $^1$H-NMR (DMSO-d$_6$) δ: 2.50-2.76 (m, 8H), 3.08-3.14 (m, 4H), 3.53 (s, 2H), 5.13 (s, 2H), 5.88 (t, J = 7.3 Hz, 1H), 6.76 (dd, J = 7.2, 7.2 Hz, 1H), 6.90-6.92 (m, 3H), 6.97 (d, J = 8.0 Hz, 1H), 7.13-7.25 (m, 4H), 7.54 (d, J = 5.0 Hz, 1H). |
| Compound 56 | $^1$H-NMR (DMSO-d$_6$) δ: 2.50-2.91 (m, 12H), 3.16-3.21 (m, 2H), 5.17 (s, 2H), 6.02-6.08 (m, 1H), 7.08-7.22 (m, 4H), 7.41-7.47 (m, 1H), 10.02 (brs, 1H), 12.13 (s, 1H). |
| Compound 57 | $^1$H-NMR (DMSO-d$_6$) δ: 2.50-2.54 (m, 2H), 2.62-2.77 (m, 10H), 3.18-3.26 (m, 2H), 5.25 (s, 2H), 5.86 (t, J = 7.0 Hz, 1H), 6.85 (d, J = 8.2 Hz, 1H), 7.05-7.20 (m, 3H), 7.53 (d, J = 5.0 Hz, 1H), 10.25 (brs, 1H), 12.12 (s, 1H). |
| Compound 58 | $^1$H-NMR (DMSO-d$_6$) δ: 1.75-1.86 (m, 4H), 2.20-2.315 (m, 2H), 2.42-2.50 (m, 2H), 2.70-2.81 (m, 2H), 2.93-3.00 (m, 6H), 5.14 (s, 2H), 5.98 (t, J = 8.0 Hz, 1H), 7.02-7.21 (m, 4H), 7.41 (d, J = 5.0 Hz, 1H). |

TABLE 7

| Compound No. | Properties |
|---|---|
| Compound 59 | $^1$H-NMR (DMSO-$d_6$) δ: 1.63-1.75 (m, 4H), 2.45-2.70 (m, 6H), 2.72-2.78 (m, 4H), 5.22 (s, 2H), 5.91 (t, J = 7.3 Hz, 1H), 6.81-6.83 (m, 1H), 7.04-7.22 (m, 3H), 7.49 (d, J = 5.0 Hz, 1H). |
| Compound 60 | $^1$H-NMR (DMSO-$d_6$) δ: 1.71-1.82 (m, 2H), 2.16-2.25 (m, 8H), 2.39 (d, J = 7.0 Hz, 2H), 2.42-2.55 (m, 2H), 2.60 (t, J = 7.5 Hz, 2H), 5.04 (s, 2H), 6.03 (t, J = 7.2 Hz, 1H), 6.77 (d, J = 5.0 Hz, 1H), 7.07-7.13 (m, 2H), 7.16 (d, J = 8.2 Hz, 1H), 7.31 (d, J = 5.0 Hz, 1H). |
| Compound 61 | $^1$H-NMR (DMSO-$d_6$) δ: 1.73-1.80 (m, 2H), 2.14-2.23 (m, 8H), 2.41-2.50 (m, 2H), 2.52-2.56 (m, 2H), 2.67 (t, J = 7.2 Hz, 2H), 5.11 (s, 2H), 5.84 (t, J = 7.2 Hz, 1H), 6.88 (d, J = 5.0 Hz, 1H), 6.96 (d, J = 7.8 Hz, 1H), 7.07-7.10 (m, 2H), 7.52 (d, J = 5.0 Hz, 1H). |
| Compound 62 | $^1$H-NMR (DMSO-$d_6$) δ: 2.28-2.30 (m, 4H), 2.41-2.45 (m, 3H), 2.55-2.58 (m, 2H), 2.63-2.66 (m, 3H), 3.58 (s, 2H), 5.06 (s, 2H), 6.09 (t, J = 7.4 Hz, 1H), 6.78 (d, J = 5.2 Hz, 1H), 7.12 (t, J = 4.2 Hz, 1H), 7.22 (s, 2H), 7.32 (d, J = 5.1 Hz, 1H). |
| Compound 63 | $^1$H-NMR (DMSO-$d_6$) δ: 2.31-2.38 (m, 4H), 2.65-2.72 (m, 8H), 3.53 (s, 2H), 5.13 (s, 2H), 5.88-5.60 (m, 1H), 6.89-6.91 (m, 1H), 6.97-6.98 (m, 1H), 7.12-7.17 (m, 2H), 7.52-7.53 (m, 1H). |
| Compound 64 | $^1$H-NMR (DMSO-$d_6$) δ: 2.07 (s, 6H), 2.11-2.42 (m, 4H), 2.50-3.22 (m, 4H), 3.51 (s, 2H), 5.99 (t, J = 6.6 Hz, 1H), 6.75 (d, J = 5.0 Hz, 1H), 7.1 (s, 1H), 7.12 (d, J = 7.5 Hz, 1H), 7.20-7.26 (m, 2H). |
| Compound 65 | $^1$H-NMR (DMSO-$d_6$) δ: 2.75 (s, 6H), 2.85-3.01 (m, 4H), 3.25-3.52 (m, 4H), 3.53 (s, 2H), 5.58-5.67 (m, 1H), 6.80-6.83 (m, 1H), 7.0-7.25 (m, 3H), 7.42-7.61 (m, 1H), 10.19 (brs, 1H), 12.31 (s, 1H). |
| Compound 66 | $^1$H-NMR (DMSO-$d_6$) δ: 1.41-1.55 (m, 8H), 1.69-1.74 (m, 2H), 1.91-1.95 (m, 2H), 2.37-2.39 (m, 4H), 2.58-2.68 (m, 4H), 2.88-2.90 (m, 2H), 3.54 (s, 2H), 5.05 (s, 2H), 6.03 (t, J = 7.2 Hz, 1H), 6.77 (d, J = 5.2 Hz, 1H), 7.10 (d, J = 8.1 Hz, 1H), 7.19-7.21 (m, 2H), 7.30 (d, J = 5.2 Hz, 1H), 8.23 (brs, 2H). |
| Compound 67 | $^1$H-NMR ($D_2O$) δ: 1.41-2.01 (m, 8H), 2.31-2.33 (m, 2H), 2.82-3.25 (m, 8H), 3.40-3.69 (m, 7H), 5.09 (s, 2H), 5.75-5.79 (m, 1H), 6.79-6.81 (m, 1H), 7.02-7.03 (m, 1H), 7.11-7.19 (m, 2H), 7.39-7.41 (m, 1H), 8.63 (brs, 2H). |

TABLE 8

| Compound No. | Properties |
|---|---|
| Compound 68 | $^1$H-NMR (DMSO-$d_6$) δ: 2.32-2.68 (m, 12H), 5.03-5.14 (m, 2H), 5.78-6.03 (m 1H), 6.76-7.82 (m, 5H). |
| Compound 69 | $^1$H-NMR (DMSO-$d_6$) δ: 1.46 (s, 6H), 1.61-1.69 (m, 4H), 2.22-3.19 (m, 12H), 5.56-5.94 (m, 1H), 6.66-6.78 (m, 1H), 7.10-7.29 (m, 4H). |
| Compound 70 | $^1$H-NMR (DMSO-$d_6$) δ: 1.82-2.00 (m, 4H), 2.58-2.66 (m, 2H), 3.12-3.18 (m, 4H), 3.15-3.23 (m, 2H), 3.62 (s, 2H), 5.07 (s, 2H), 6.01 (t, J = 7.4 Hz, 1H), 6.80 (d, J = 5.2 Hz, 1H), 7.13 (d, J = 8.0 Hz, 1H), 7.20-7.58 (m, 2H), 7.36 (d, J = 5.2 Hz, 1H). |
| Compound 71 | $^1$H-NMR (DMSO-$d_6$) δ: 1.82-2.02 (m, 4H), 2.93-3.04 (m, 4H), 3.29-3.38 (m, 2H), 3.52-3.55 (m, 4H), 5.15 (s, 2H), 5.82 (t, J = 7.2 Hz, 1H), 6.93 (d, J = 5.2 Hz, 1H), 7.00 (d, J = 8.2 Hz, 1H), 7.17-7.22 (m, 2H), 7.60 (d, J = 5.2 Hz, 1H), 10.56 (brs, 1H), 12.33 (s, 1H). |

Example 56

In Vitro Human Histamine H1 Receptor Binding Experiment

Recombinant human histamine H1 receptor plasmid (prepared by Invitrogen) was transfected to HEK293A cells with Lipofectamine 2000 (Invitrogen). Cells stably expressing human histamine H1 receptor were screened with Geneticin (Invitrogen). The cells were continued to be cultured using a Dulbecco's Modified Eagle Medium containing 10% fetal bovine serum, 0.1 mmol/L MEM Non-Essential Amino Acids Solution, 2 mmol/L L-glutamine and 0.7 mg/mL Geneticin in a 5% $CO_2$ incubator at 37° C. The cells stably expressing human histamine H1 receptor were prepared using 50 mmol/L Tris-HCl (pH 7.5) (hereinafter referred to as buffer) containing 0.1% bovine serum albumin, so as to have a concentration of $3 \times 10^6$ cells/mL, to give a cell sample preparation. Fifty microliters of the buffer, 50 μL of a test substance solution at various concentrations, and 50 μL of [$^3$H]pyrilamine solution (final concentration: 3 nmol/L) were added to each of the wells on the 96-well plate, and stirred, and 100 μL of the cell sample preparation was then added thereto (at a concentration of $3 \times 10^5$ cells/well) to initiate the reaction.

The cells were incubated at room temperature for 60 minutes, and then filtered on UniFilter GF/C plate (Packard) immersed in 0.5% polyethyleneimine using a cell harvester (IH-110, INNOTECH CORPORATION), to stop the reaction, and the plate was washed with the buffer. The plate after washing was sufficiently dried, and 20 μL of a scintillator (MaxiLight, manufactured by Hidex) was added thereto, and count per minute (cpm) was measured with a multi-labeled microplate reader (Plate Chameleo II, Hidex). The nonspecific binding was cpm in a case where 30 μmol/L pyrilamine was added. The experiments were carried out at n=3, and at least repeated 3 times.

One example of the results are shown in Table 9. The compounds of the present invention showed very high potent activity in in vitro human histamine H1 receptor binding experiment.

TABLE 9

| Compound No. | $IC_{50}$ (nmol/L) |
|---|---|
| Compound 3 | 22.2 |
| Compound 9 | 55.7 |
| Compound 13 | 32.4 |
| Compound 19 | 56.9 |
| Compound 21 | 74.7 |
| Compound 22 | 60.0 |
| Compound 23 | 74.6 |
| Compound 24 | 13.2 |
| Compound 26 | 19.2 |
| Compound 27 | 70.2 |
| Compound 28 | 43.4 |
| Compound 29 | 70.7 |
| Compound 30 | 57.6 |
| Compound 34 | 31.4 |
| Compound 40 | 19.1 |
| Compound 42 | 99.8 |
| Compound 50 | 89.1 |
| Compound 54 | 10.9 |
| Compound 55 | 19.6 |
| Compound 56 | 29.0 |
| Compound 57 | 56.3 |
| Compound 58 | 23.0 |
| Compound 59 | 36.0 |
| Compound 62 | 60.5 |
| Compound 64 | 8.56 |
| Compound 65 | 14.0 |
| Compound 66 | 31.2 |
| Compound 68 | 45.2 |
| Compound 69 | 53.8 |
| Compound 70 | 14.3 |
| Compound 71 | 63.4 |

Example 57

Rat Histamine-Induced Vascular Hypermeability Reaction (In Vivo Antihistamine Action)

An SD male rat (SPF) of 180 g in weight was previously fed for one week or more by allowing the rat to take a solid feed and tap water ad libitum, under the environment setting of a temperature of 22° C., humidity of 55% and an artificial illumination of 12 hours a day (light phase 8 am to 8 pm), and the rat was fasted overnight to be used for the experiment. Histamine.dihydrochloride (hereinafter referred to as histamine) and Evans Blue were used by dissolving each in physiological saline upon use. A substance to be tested was dissolved in water for injection or suspended in 0.5% carboxymethyl cellulose sodium, and the rat was orally administered with the solution or suspension (dose volume: 5 mL/kg body weight). After 1 hour from the administration, the physiological saline and the histamine solution were each intracutaneously injected to two locations (20 μg/0.05 ml/location) each on a back part of the rat of which hair was sheared with an electric clipper while anesthetizing with an ether. A 0.5% Evans Blue-containing physiological saline was injected into the tail vein of the rat (1 mL/200 g body weight) immediately before the intracutaneous injection of the histamine.

After 30 minutes, the animal was decapitated, and exsanguinated, and the skin was removed to measure an amount of leaked pigment in the blue-stained portion. The measurement of the amount of leaked pigment was carried out as follows. Skins of the pigment leaking site were cut out at two locations, 1 mL of a 2 mol/L aqueous potassium hydroxide solution was added thereto in a test tube, and the test tube was allowed to stand overnight at 37° C. to dissolve. Thereafter, 6 mL of a 1:3 mixed solution of 0.67 mol/L phosphoric acid and acetone was added to the solution, and the mixture was vigorously shaken for 10 minutes. Thereafter, the mixture was filtered, and the absorbance of the filtrate at 620 nm was measured. The absorbance obtained from the two locations of the sites injected with physiological saline, as blank value, was used for a compensation. The amount of leaked pigment was calculated from the calibration curve of Evans Blue at 620 nm.

One example of the results is shown in Table 10. The compound of the present invention showed a very potent antagonistic activity in the rat histamine-induced vascular hyperpermeability reaction.

Example 58

Murine Cerebral H1 Receptor Occupying Content (Ex Vivo)

A 6-week-old ICR male mouse was previously fed for one week or more by allowing the mouse to take a solid feed and tap water ad libitum, under the environment setting of a temperature of 22° C., humidity of 55% and an artificial illumination of 12 hours a day, and the mouse was fasted overnight to be used for the experiment. A substance to be tested was dissolved with water for injection or suspended in 0.5% carboxymethyl cellulose solution, and the solution or suspension was orally administered to the mouse (dose volume: 0.1 mL/10 g body weight). After 1 hour from the oral administration, the mouse was decapitated, and the entire brain, except for cerebellum and medulla oblongatae, was rapidly excised. The excised brain tissue was homogenized with Polytron (Kinematica) in an ice-cooled 50 mmol/L phosphate buffered saline (pH 7.4, 100 mg/1.9 mL).

To a test tube for reaction (TPX-Tube) were added 180 μL of the brain homogenate, and 10 μL of $^3$H-pyrilamine solution (final concentration: 2 nmol/L) and 10 μL of a non-labeled pyrilamine solution (final concentration: 200 μmol/L) or a 50 mmol/L phosphate buffered saline, and the mixture was incubated at room temperature for 45 minutes, and 2.0 mL of an ice-cooled, 50 mmol/L phosphate buffered saline was then added thereto to stop the reaction. The reaction mixture was filtered with a GF/B filter (ADVANTEC), and the filtrate was placed in a vial and dried overnight at 60 degrees. After drying, 10 mL of a scintillator (AL-1, toluene-based, DOJINDO LABORATORIES) was added to the product, and the disintegration per minute (dpm) was measured with a liquid scintillation counter (Packard, U.S.A., TRI-CARB 2700TR) (5 minutes/vial).

One example of the results is shown in Table 11. In this experiment, the compound of the present invention require a high concentration for occupying the receptor in the brain, showing that the brain transfer is low. It was evident from the results that the compounds of the present invention show peripheral-selective anti-histamine action without undergoing brain transfer, so that the compounds can alleviate side effects on the central nervous system, such as drowsiness.

TABLE 10

| Compound No. | $ED_{50}$ (mg/kg) |
| --- | --- |
| Compound 16 | 0.299 |
| Compound 18 | 0.063 |
| Compound 19 | 0.24 |
| Compound 20 | 0.45 |
| Compound 22 | Ca. 1 |
| Compound 24 | Ca. 1 |
| Compound 25 | 5.70 |
| Compound 26 | 0.156 |
| Compound 27 | 0.226 |
| Compound 28 | <0.1 |
| Compound 29 | <0.1 |
| Compound 30 | Ca. 0.3 |
| Compound 31 | Ca. 1 |
| Compound 33 | Ca. 0.3 |
| Compound 34 | Ca. 0.3 |
| Compound 35 | Ca. 0.1 |
| Compound 43 | 1.31 |
| Compound 50 | 1.34 |
| Compound 57 | Ca. 0.1 |
| Compound 58 | Ca. 0.1 |
| Compound 59 | Ca. 0.3 |
| Compound 70 | 0.42 |
| Compound 71 | 0.83 |
| Ketotifen | 0.54 |

TABLE 11

| Compound No. | $ID_{50}$ (mg/kg) |
| --- | --- |
| Compound 16 | 45.8 |
| Compound 18 | 2.1 |
| Compound 19 | 6.08 |
| Compound 20 | 109.3 |
| Compound 22 | 18.7 |
| Compound 24 | 174.0 |
| Compound 25 | >200 |
| Compound 26 | 80.9 |
| Compound 27 | >200 |
| Compound 28 | 5.85 |
| Compound 29 | 23.7 |
| Compound 30 | 95.0 |
| Compound 31 | >200 |
| Compound 33 | 21.1 |
| Compound 34 | 34.8 |
| Compound 35 | 65.7 |
| Compound 43 | >80 |
| Compound 50 | >80 |
| Compound 57 | >80 |
| Compound 58 | 110.2 |
| Compound 59 | >200 |
| Compound 70 | 51.4 |
| Compound 71 | >80 |
| Ketotifen | 0.51 |

From the results of Examples 57 and 58 mentioned above, the values obtained by dividing the $ID_{50}$ (Table 11) of the cerebral receptor binding test by the $ED_{50}$ (Table 10) of the histamine-induced vascular hyperpermeability reaction test are shown in Table 12. The larger the $ID_{50}$ (Table 11) of the cerebral receptor binding test, the lower the brain transfer, i.e. the smaller the side effects on the central nervous system, such as drowsiness; and the smaller the $ED_{50}$ (Table 10) of the histamine-induced vascular hyperpermeability reaction test, the more potent the antihistamine action. Therefore, the value calculated by $ID_{50}/ED_{50}$ can serve as an index showing that the larger the calculated value, the more potent the antihistamine action and the smaller the side effects on the central nervous system, such as drowsiness. As shown in Table 12, the compound of the present invention shows a large value for a value calculated by $ID_{50}/ED_{50}$, as compared to an already existing antihistamine Ketotifen. Therefore, it can be said that the compound of the present invention has desired properties as a pharmaceutical composition, especially as an active ingredient for antihistamine, that has a potent antihistamine action and smaller side effects on the central nervous system, such as drowsiness.

TABLE 12

| Compound No. | $ID_{50}$ (mg/kg)/ $ED_{50}$ (mg/kg) |
|---|---|
| Compound 16 | 153.2 |
| Compound 18 | 33.3 |
| Compound 19 | 25.3 |
| Compound 20 | 242.9 |
| Compound 22 | 18.7 |
| Compound 24 | 174.0 |
| Compound 25 | >35.1 |
| Compound 26 | 518.6 |
| Compound 27 | >885 |
| Compound 28 | >58.5 |
| Compound 29 | >237 |
| Compound 30 | 316.7 |
| Compound 31 | >200 |
| Compound 33 | 70.3 |
| Compound 34 | 116.0 |
| Compound 35 | 657.0 |
| Compound 43 | >61.1 |
| Compound 50 | >59.7 |
| Compound 57 | >800 |
| Compound 58 | 110.2 |
| Compound 59 | >666.7 |
| Compound 70 | 122.4 |
| Compound 71 | >96.4 |
| Ketotifen | 0.9 |

INDUSTRIAL APPLICABILITY

The aminopropylidene derivative of the present invention had a potent histamine H1 receptor binding ability as shown in Table 9, and showed a potent histamine receptor antagonistic activity in the rat histamine-induced vascular hyperpermeability reaction, as shown in Table 10. Further, as is clear from Table 11, the aminopropylidene derivative shows a low brain transfer even in a cerebral receptor binding test where a mouse is orally administered, so that the aminopropylidene derivative of the present invention is preferable from the aspect of alleviating side effects on the central nervous system, such as drowsiness. As is clear from the values of Table 12 for together evaluating both of these histamine receptor antagonistic activity and brain transfer, the aminopropylidene derivative of the present invention is a potent histamine receptor antagonistic substance, and has smaller side effects on the central nervous system, such as drowsiness; therefore, the aminopropylidene derivative has properties suitable for an active ingredient of a pharmaceutical composition, such as a desired antihistamine, so that the aminopropylidene derivative is highly useful.

The invention claimed is:

1. An aminopropylidene derivative, or salt or hydrate thereof that is pharmaceutically acceptable, wherein the aminopropylidene derivative is represented by the following general formula (I):

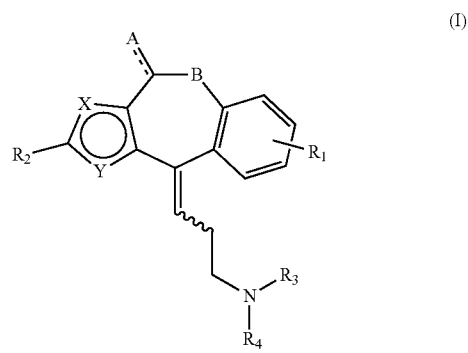

wherein $R_1$ and $R_2$, which may be identical or different, stand for a hydrogen or a substituent selected from the following (a) to (c) with proviso that a case where both are hydrogen is excluded:
(a) a carbonyl substituted with hydroxy, alkoxy, or hydroxyalkylamino,
(b) a carbonylalkyl substituted with hydroxy or alkoxy, and
(c) acrylic acid or an alkyl ester of acrylic acid,
$R_3$ and $R_4$, which may be identical or different, stand for hydrogen,
an alkyl which may be substituted with phenyl, or
a cycloalkyl, or
$R_3$ and $R_4$, which together form a heterocyclic ring with a nitrogen atom bonded thereto, stand for a pyrrolidino, a piperidino which may be substituted with oxo or piperidino, a piperadinyl substituted with alkyl or phenyl, a morpholino, or a thiomorpholino,
A stands for unsubstituted or an oxo, B stands for a carbon or an oxygen, one of X and Y stands for a carbon and the other stands for a sulfur, a broken line part stands for a single bond or a double bond, and a wavy line stands for cis-form and/or trans-form.

2. The aminopropylidene derivative, or salt or hydrate thereof that is pharmaceutically acceptable according to claim 1, wherein A is unsubstituted.

3. The aminopropylidene derivative, or salt or hydrate thereof that is pharmaceutically acceptable according to claim 2, wherein B is an oxygen.

4. The aminopropylidene derivative, or salt or hydrate thereof that is pharmaceutically acceptable according to claim 3, wherein $R_2$ is a hydrogen.

5. The aminopropylidene derivative, or salt or hydrate thereof that is pharmaceutically acceptable according to claim 4, wherein X is a carbon and Y is a sulfur.

6. The aminopropylidene derivative, or salt or hydrate thereof that is pharmaceutically acceptable according to claim 5, wherein $R_1$ is a carbonylalkyl substituted with hydroxy.

7. The aminopropylidene derivative, or salt or hydrate thereof that is pharmaceutically acceptable according to claim 1, wherein the aminopropylidene derivative represented by the general formula (I) is a compound selected from (E)-{4[3-(pyrrolidin-1-yl)propylidene]-4,10-dihydro-9-oxa-3-thiabenzo[f]azulen-6-yl}acetic acid, (Z)-{4-[3-(pyrrolidin-1-yl)propylidene]-4,10-dihydro-9-oxa-3-thiabenzo[f]azulen-6-yl}acetic acid, (E)-[4-(3-ethylmethylaminopropylidene)-4,10-dihydro-9-oxa-3-thiabenzo[f]azulen-6-yl]acetic acid, (Z)-[4-(3-ethylmethylaminopropylidene)-4,10-dihydro-9-oxa-3-thiabenzo[f]azulen-6-yl]acetic acid, (E)-{4-[3-(piperidin-1-yl)propylidene]-4,10-dihydro-9-oxa-3-thiabenzo[f]azulen-6-yl}acetic acid, (Z)-{4-[3-(piperidin-1-yl)propylidene]-4,10-dihydro-9-oxa-3-thiabenzo[f]azulen-6-yl}acetic acid, (Z)-[4-(3-benzylaminopropylidene)-4,10-dihydro-9-oxa-3-thiabenzo[f]azulen-6-yl]acetic acid, and (E)-{4-[3-(4-methylpiperadin-1-yl)propylidene]-4,10-dihydro-9-oxa-3-thiabenzo[f]azulen-6-yl}acetic acid.

8. A pharmaceutical composition comprising at least one member of the aminopropylidene derivatives, and salt and hydrate thereof that are pharmaceutically acceptable as defined in claim 1.

9. The pharmaceutical composition according to claim 8, which is an antihistamine.

10. A method for treating at least one disease selected from bronchial asthma, allergic rhinitis, pollinosis, urticaria, and atopic dermatitis, comprising administering to a patient in need of such treatment at least one member selected from the aminopropylidene derivatives, or salt or hydrate thereof that is pharmaceutically acceptable as defined in claim 1 in an effective dose.

11. A pharmaceutical composition comprising at least one member of the aminopropylidene derivatives, and salt and hydrate thereof that are pharmaceutically acceptable as defined in claim 2.

12. A pharmaceutical composition comprising at least one member of the aminopropylidene derivatives, and salt and hydrate thereof that are pharmaceutically acceptable as defined in claim 3.

13. A pharmaceutical composition comprising at least one member of the aminopropylidene derivatives, and salt and hydrate thereof that are pharmaceutically acceptable as defined in claim 4.

14. A pharmaceutical composition comprising at least one member of the aminopropylidene derivatives, and salt and hydrate thereof that are pharmaceutically acceptable as defined in claim 5.

15. A pharmaceutical composition comprising at least one member of the aminopropylidene derivatives, and salt and hydrate thereof that are pharmaceutically acceptable as defined in claim 6.

16. A pharmaceutical composition comprising at least one member of the aminopropylidene derivatives, and salt and hydrate thereof that are pharmaceutically acceptable as defined in claim 7.

17. The pharmaceutical composition according to claim 11, which is an antihistamine.

18. The pharmaceutical composition according to claim 12, which is an antihistamine.

19. The pharmaceutical composition according to claim 13, which is an antihistamine.

20. The pharmaceutical composition according to claim 14, which is an antihistamine.

21. The pharmaceutical composition according to claim 15, which is an antihistamine.

22. The pharmaceutical composition according to claim 16, which is an antihistamine.

\* \* \* \* \*